(12) United States Patent
Cairns et al.

(10) Patent No.: US 10,662,409 B2
(45) Date of Patent: May 26, 2020

(54) METHODS OF GENERATING NEURAL STEM CELLS

(71) Applicant: Trustees of Tufts College, Medford, MA (US)

(72) Inventors: Dana Cairns, Somerville, MA (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 111 days.

(21) Appl. No.: 15/757,056

(22) PCT Filed: Sep. 9, 2016

(86) PCT No.: PCT/US2016/051112
§ 371 (c)(1),
(2) Date: Mar. 2, 2018

(87) PCT Pub. No.: WO2017/044853
PCT Pub. Date: Mar. 16, 2017

(65) Prior Publication Data
US 2018/0258389 A1    Sep. 13, 2018

Related U.S. Application Data

(60) Provisional application No. 62/216,037, filed on Sep. 9, 2015.

(51) Int. Cl.
| | | |
|---|---|---|
| *C12N 5/00* | (2006.01) | |
| *C12N 5/0797* | (2010.01) | |
| *C12N 15/67* | (2006.01) | |
| *C12N 15/85* | (2006.01) | |
| *C12N 15/63* | (2006.01) | |
| *C12N 5/10* | (2006.01) | |

(52) U.S. Cl.
CPC ............ *C12N 5/0623* (2013.01); *C12N 5/10* (2013.01); *C12N 15/63* (2013.01); *C12N 15/67* (2013.01); *C12N 15/85* (2013.01); *C12N 2740/15041* (2013.01)

(58) Field of Classification Search
CPC .............................. C12N 5/0623; C12N 15/63
See application file for complete search history.

(56) References Cited

U.S. PATENT DOCUMENTS

| | | | |
|---|---|---|---|
| 2010/0158880 A1 | 6/2010 | Seyda et al. | |
| 2014/0315988 A1* | 10/2014 | Dahl | C12N 5/0696 514/44 R |
| 2015/0118755 A1* | 4/2015 | Jaenisch | C07K 14/4702 435/462 |

FOREIGN PATENT DOCUMENTS

WO    WO-2010/141801 A2    12/2010

OTHER PUBLICATIONS

Their et al. Cell Stem Cell 10:473-479, 2012 (Year: 2012).*
Kim et al. PNAS 108(19):7838-7843, 2011 (Year: 2011).*
Li et al. Cell Stem Cell 4:16-19, 2009 (Year: 2009).*
Cheng et al. Cell Research 24:665-679, 2014. (Year: 2014).*
Ebert et al., "Induced Pluripotent Stem Cells from a Spinal Muscular Atrophy Patient," Nature, 457(7227):277-280 (2009).
International Search Report and Written Opinion for International Application No. PCT/US2016/51112 dated Dec. 20, 2016.
Sharow et al., "Retinoic Acid Stability in Stem Cell Cultures," Int J Dev Biol, 56(4):273-278 (2012).

\* cited by examiner

*Primary Examiner* — Marcia S Noble
(74) *Attorney, Agent, or Firm* — Foley Hoag LLP

(57) ABSTRACT

In some embodiments, the present invention provides methods including the steps of providing one or more human somatic cells, causing transient increased expression of OCT4, KLF4, SOX2, and cMYC in the somatic cells forming modified somatic cells, providing a plurality of inactivated embryonic fibroblasts, associating the modified somatic cells with the inactivated embryonic fibroblasts in a culture media comprising 20% KO DMEM xeno-free serum replacement and at least 15 ng/ml recombinant bFGF to form human induced neural stem cells.

20 Claims, 17 Drawing Sheets

Specification includes a Sequence Listing.

SEQUENCE LISTING

<160> NUMBER OF SEQ ID NOS: 36

<210> SEQ ID NO 1
<211> LENGTH: 19
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 1
aaaccctggc acaaactcc                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacatgtccc agcactacc                                                    19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccttgcaaa tgtcttctgc t                                                 21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccgttggaa ctgatggagt                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
attattttgc ccgttttccc                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttttcaagct ccctgcagtt                                                   20

<210> SEQ ID NO 7
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
tggtttacgc tacttttggg g                                              21

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctggcgtccg agtccat                                                   17

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgaaggagt gtctggtgat g                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcaggaccac aggcaataaa                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttctcagccg caaactatcc                                                20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttttggattc atatgccttc tgt                                            23

<210> SEQ ID NO 13
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 13
agaactcccg gctgcaaac                                                    19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
actctccaac gctgatctcc                                                   20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctcaggggc ctttggacat ctctt                                             25

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaccacctcg ccttacacat                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tacgtgttca tgccgttcat                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccctatgctc atcggaacaa                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 19
gaccagtgtc ctttcctctg                                            20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccatgctgtt tcttactctc ctc                                        23

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagggctgtc ctgaataagc                                            20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttggtatcc ggggacttc                                             19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcaaggaaac acaatcgctg                                            20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agggaccatt gcaacttttg                                            20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccagtgtttt gtcgcagaga                                                    20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctgaggctt ttcggagc                                                      18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gattgcgcca gcactttatc                                                    20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaccggggt tgtcaaaaa                                                     19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ataacgaggc tgtggagcag                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acccattggc attctctttg                                                    20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 31
tctggggtcc tagggaattg                                          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cagccagcag attacaatgc                                          20

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttttcacact ccttccgcac cacatc                                   26

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttcagctccg tctccatcat                                          20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgactggagc agctactatg c                                        21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caattgtcat gggattgcag                                          20
```

METHODS OF GENERATING NEURAL STEM CELLS

GOVERNMENT SUPPORT

This invention was made with government support under grant number EB002520 awarded by the National Institutes of Health. The government has certain rights in the invention.

BACKGROUND

Much of our understanding of the human nervous system is derived from animal models, as well as basic in vitro monoculture of human neural cell types. Clearly, these model systems cannot truly recapitulate the human condition, given the complexity of the human brain or the variety of innervated tissues of the peripheral nervous system. As such, there is a critical need to develop more physiologically relevant in vitro human models of the brain and multi-tissue innervated co-cultures, for the purpose of high throughput analysis, the study of various cell-cell interactions, and the development of relevant disease models. Additionally, the establishment of robust models of human nervous tissue development may lead, directly or indirectly, to significant therapeutic advances.

SUMMARY OF THE INVENTION

The present invention is based, in part, on the surprising discovery that human induced neural stem cells (hiNSCs) may be created from any human somatic cell (not only those of ectodermal origin) and that the hiNSCs are able to be passaged indefinitely without losing proliferative and/or differentiation capacities (i.e., a substantially undiminished capacity for self-renewal). In other words, cells produced by provided methods may be clonally reproduced indefinitely without suffering from the cell death or spontaneous differentiation observed in cells produced by previous methods.

In addition, according to various embodiments, provided hiNSCs produced by provided methods are able to be differentiated into neurons and/or glia without the need to form an intermediate neurosphere (which are known to be non-adherent), a common and cumbersome step required in previous methods. For the purposes of tissue engineering avoiding neurosphere formation is ideal because once cells have been equilibrated to low adhesion conditions, the transition to adherent monolayer or 3D culture is sometimes difficult. Furthermore, the center part of neurospheres can often become necrotic.

An additional advantage provided by various embodiments is the ability for provided hiNSCs to maintain their resultant neuronal or glial phenotype, even in a mixed culture of cells. In some embodiments, provided hiNSCs are able to be cultured in a three dimensional matrix, for example, in a three dimensional model of a human cerebral cortex.

In some embodiments, the present invention provides methods including the steps of providing one or more human somatic cells, causing transient increased expression of octamer-binding transcription factor 4 (OCT4), Kruppel-like factor 4 (KLF4), SRY (Sex-determining region Y) box 2 (SOX2), and cMYC in the somatic cells forming modified somatic cells, providing a plurality of inactivated embryonic fibroblasts, associating the modified somatic cells with the inactivated embryonic fibroblasts in a culture media comprising 20% KO DMEM xeno-free serum replacement and at least 15 ng/ml recombinant bFGF to form human induced neural stem cells. In some embodiments, the inactivated embryonic fibroblasts are associated with the modified somatic cells in a culture media comprising 20% KO DMEM xeno-free serum replacement and at least 20 ng/ml recombinant bFGF.

In some embodiments, provided methods further include the step of dissociating the human induced neural stem cells from the inactivated embryonic fibroblasts, wherein the dissociation causes the human induced neural stem cells to become at least one of neurons and glial cells. In some embodiments, the dissociated human induced neural stem cells are exposed to one or more of retinoic acid and 10 ng/ml or less bFGF. In some embodiments, the dissociated human induced neural stem cells are exposed to retinoic acid at a concentration between about 10 to about 100 µM.

In some embodiments, provided methods further include culturing neurons, which neurons arise from dissociating human induced neural stem cells, with one or more of retinoic acid (RA), sonic hedgehog (Shh), and fibroblast growth factor 8 (FGF8). In some embodiments, the final concentration of each of the RA, Shh, and/or FGF8 in the culture is between about 10 to about 100 µM. In some embodiments, culturing of the neurons with at least one of RA and Shh results in directed differentiation into a motor neuron subtype. In some embodiments, culturing the neurons with at least one of FGF8 and Shh results in directed differentiation into a dopaminergic neuron subtype.

In some embodiments, provided methods further include the step of associating the dissociated human induced neural stem cells with a plurality of non-neuronal cells. In some embodiments, the association with non-neuronal cells results in innervation of at least some of the non-neuronal cells.

According to various embodiments, any of a variety of methods may be used to cause increased transient expression of OCT4, KLF4, SOX2, and cMYC in the somatic cells. In some embodiments, the transient increased expression is caused by a vector. In some embodiments, the vector is a polycistronic vector. In some embodiments, the polycistronic vector is a lentivirus. In some embodiments, the transient expression is caused by at least one of a small molecule and a nucleic acid.

According to various embodiments, any of a variety of inactivated embryonic fibroblasts may be used. In some embodiments, the plurality of inactivated embryonic fibroblasts are inactivated mouse embryonic fibroblasts.

In some embodiments, any method of inactivating embryonic fibroblasts may be used in an application-appropriate manner. In some embodiments, the mouse embryonic fibroblasts are inactivated via one or more of mitomycin C treatment and gamma irradiation.

Provided methods provide powerful new ways to modify any human somatic cell. In some embodiments, the human somatic cells are adult human somatic cells. In some embodiments, the human somatic cells are neonatal human somatic cells. In some embodiments, the human somatic cells are selected from the group consisting of fibroblasts, adipocytes, dermal cells, epidermal cells, muscle cells, or bone cells.

While previous methods have been developed for the direct reprogramming of human induced neural stem cells, these strategies do not allow for efficient expansion of the cells as clonal lines, and as a result, the reprogramming process must be continually repeated in order to in order generate enough cells with which to perform subsequent experiments. While some of these methods have demonstrated that their lines can be expanded, it is often only for a few passages (i.e, <7), with the capacity for self-renewal and neurogenesis decreasing upon each passage. Accordingly, in some embodiments, provided methods allow for previously unattainable levels of self-renewal. In some embodiments, provided human induced neural stem cells are able to be maintained for at least one year prior to dissociation. In some embodiments, provided human induced neural stem cells are able to be maintained for at least two years prior to dissociation. In some embodiments, provided human induced neural stem cells may be passaged at least 15 times while associated with the inactivated mouse embryonic fibroblasts without substantial differentiation of the human induced neural stem cells occurring.

In some embodiments, during the reprogramming of provided somatic cells, at least two of OCT4, KLF4, SOX2, and cMYC are transiently expressed in a particular stoichiometric range or proportion. For example, in some embodiments, OCT4, KLF4, SOX2, and cMYC are transiently expressed in approximately a 1:1:1:1 ratio. In some embodiments, at least two of OCT4, KLF4, SOX2, and cMYC are transiently expressed in approximately a 1:1 ratio. In some embodiments, OCT4, KLF4, SOX2, and cMYC are transiently expressed in approximately a ratio other than a 1:1:1:1 ratio. In some embodiments, OCT4, KLF4, SOX2 are transiently expressed in approximately a 1:1:1 ratio, and cMYC is expressed at a lower ratio as compared to OCT4, KLF4, and/or SOX2.

In some embodiments, provided methods allow for freezing and thawing of provided human induced neural stem cells without substantial loss of at least one of proliferation capacity and differentiation capacity. In some embodiments, provided human induced neural stem cells are able to be frozen and thawed at least once and maintain at least a 90% proliferation capacity. In some embodiments, provided human induced neural stem cells are able to be frozen and thawed at least five times and maintain at least a 50% proliferation capacity. In some embodiments, proliferation capacity is measured via at least one of Ki67 immunostaining, a BrdU incorporation assay, a Resazurin or other redox-based assay, and a growth curve/measure of doubling time. In some embodiments, provided human induced neural stem cells are able to be frozen and thawed at least once with substantially no loss in differentiation capacity. In some embodiments, provided human induced neural stem cells are able to be frozen and thawed at least five times with substantially no loss in differentiation capacity. In some embodiments, differentiation capacity is measured via at least one immunostaining assay, for example, Tuj1 immunostaining. In some embodiments, differentiation capacity is measured via at least one fluorescence-based assay, for example, a luciferase-based assay (e.g., an assay such as that described in Hughes, D., et al (2012), Characterization of early phenotypic changes in differentiating NCCIT cells using multiplexed luciferase reporters and immunofluorescence in/aging Poster #633.25. Presented Tuesday, Oct. 16, 2012. Society for Neuroscience Annual Meeting. New Orleans, La.). In some embodiments, both proliferation capacity and differentiation capacity may be measured using the same assay or kit. Exemplary non-limiting kits that may be used according to some embodiments include the Neural Precursor Cell-Based Screening & Bioassay Kit (R&D Systems # SC014)

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The foregoing and other objects, aspects, features, and advantages of the present disclosure will become more apparent and better understood by referring to the following description taken in conduction with the accompanying drawing, in which:

FIG. 1A depicts an exemplary protocol for generating hiNSCs. FIG. 1B illustrates two aspects of the invention, namely, that hiNSCs may proliferate multiple times, cultured as colonies on MEF feeders in the presence of high levels of FGF and that hiNSCs may be encouraged to spontaneously differentiate into neurons and glia. In some embodiments, these two aspects may occur in parallel within the same culture.

FIG. 2A shows H1 hESC colonies express all pluripotent markers Oct4, Sox2, Nanog, SSEA4 and Tra-1-81. In some embodiments, most or all reprogrammed hiNSC clonal lines express markers Oct4, Sox2 and Nanog, but do not express cell surface markers of pluripotency, SSEA4 and Tra-1-81 (scale bar, 100 μM). FIG. 2B shows an exemplary gene expression profile comparing H1 hESC to hiNSC clonal lines. Unlike hESC, hiNSC lines do not upregulate endogenous Oct4. FIG. 2C shows exemplary morphology of hESC colonies compared to hiNSC colonies. While both colony types are round, with clearly defined edges, hiNSC colonies exhibit a more domed morphology (scale bar, 100 μM).

FIG. 3A shows that Ki67 immunostaining reveals that a large percentage of cells within the hiNSC colonies are positive for proliferation (scale bar 100 μm). FIG. 3B shows exemplary photographs illustrating that hiNSCs express various neural stem cell markers (e.g., Pax6, Sox1, Nestin and CD133; scale bar 100 μm). FIG. 3C shows an exemplary gene expression profile comparing expression of NSC markers in commercially available human NSC lines to those of hiNSC clonal lines (scale bar 100 μm).

FIG. 4A shows exemplary photographs and graphs demonstrating that expression of neuron-specific beta-1 11-tubulin (TUJI) and glial fibrillary acidic (GFAP) in hiNSC clonal lines derived from hFF and hASC at 4 and 14 days. As early as 4 days, over 80% of cells stain positive for neuron markers. Nuclei are marked with DAPI. Insets in each panel show single channel labeling for TUJI and GFAP. FIG. 4B shows exemplary photographs demonstrating that provided hiNSCs spontaneously differentiate into multiple subtypes of neurons including GABAergic and glutamatergic. Embryonic rat brain-derived neurons, another cell type commonly used in tissue engineering, are shown as a positive control. FIG. 4C shows exemplary photographs demonstrating that provided hiNSCs express post-synaptic proteins at both inhibitory (gephyrin and VGAT) and excitatory (PSD95 and VGLUT I synapses. FIG. 4D shows exemplary photographs demonstrating that provided hiNSCs spontaneously express synaptic vesicle protein, synaptophysin, as well as the voltage-gated sodium channel marker pan-NaV, suggestive of their ability to elicit action potentials. FIG. 4E shows exemplary photographs demonstrating that provided hiNSCs in long term culture also spontaneously differentiate into multiple types of glia including astrocytes (GFAP), oligodendrocytes(04), myelin marker positive glia (MBP) surrounding neurons, and microglia (Iba-I). FIG. 4F shows exemplary photographs demonstrating that provided hiNSCs are able to survive and maintain neuronal and glial phenotypes in long term cultures.

FIG. 5A shows an exemplary bright field image of hiNSC colonies that had been removed from feeders, dissociated and cultured for one week on gelatin. FIG. 5B shows an exemplary calcium imaging of provided hiNSCs, demonstrating active calcium signaling as early as one week. FIG. 5C shows exemplary electrophysiology recordings of provided hiNSCs cultured for 1 week demonstrating that the cells have functional GABA receptors that depolarize in response to the GABA agonist, muscimol. FIG. 5D shows exemplary graphs of calcium signaling of provided hiNSCs in response to picrotoxin, which is increased noticeably at two weeks of culture. Picrotoxin blocks inhibitory GABA receptors thereby activating excitatory neuronal firing. This demonstrates that hiNSCs can respond to pharmaceutical agents in a physiologically relevant manner. FIG. 5E shows an exemplary bright field image of provided hiNSC colonies that have been removed from feeders, dissociated, and cultured for eight weeks on poly-L-lysine coated coverslips. FIGS. 5F & 5G shows that patch clamp electrophysiological measures demonstrate that provided hiNSCs cultured for 8 weeks elicit both current-induced (FIG. 5F) as well as spontaneous (FIG. 5G) action potentials.

FIG. 6A is a schematic illustration of an exemplary injection method. Embryos were then harvested between 1-8 days for subsequent analysis. FIG. 6B shows that fluorescently labeled hiNSCs localize to the cranial region 24 hours post-injection (arrowhead shows localization of fluorescent DiD-labeled cells localized in the cranial region of the embryo) Scale bars, 500 µm. FIGS. 6C, 6E and 6F are exemplary images of embryos harvested at six days post-injection, with the developing limbs cryosectioned. Rectangular outlines in FIG. 6E identify magnified areas in FIG. 6F. FIG. 6F shows exemplary immunostaining results, revealing the presence of human cells as indicated by human nuclear antigen (HUNU) immunostaining, which co-localizes with Nestin (a neural stem cell marker), HB9 (a marker of developing motor neurons), and NF (neurofilament of sensory and motor axons) in the developing limb, suggesting that hiNSCs retain their neuronal phenotype, and can migrate and contribute to the peripheral nervous system (arrowheads in FIG. 6 point to cells in the limb bud that co-express HUNU and Nestin, HB9 or NF). Scale bar, 500 µm in 6E and 100 µm 6F. FIGS. 6D, 6G and 6H show exemplary images of embryos harvested at 8 days post-injection, and the head region cryosectioned. FIGS. 6G and 6H show exemplary immunostaining results, revealing the presence of HUNU-positive cells, which co-localized with TUJ1 (a later stage marker of neuronal differentiation) as well as neuronal subtype-specific markers VGAT (GABAergic) and VGLUT2 (glutamatergic) in the developing brain, suggesting that hiNSCs can differentiate in vivo to contribute to the developing central nervous system (arrowheads in FIG. 6H point to cells in the developing brain that co-express HUNU Tuj1, VGAT, and/or VGLUT2). Scale bars, 1 mm in 6G and 100 µm 6H FIG. 7A shows exemplary images of provided hiNSCs differentiating into mostly neuronal and glial phenotypes in various media types, as well as a graph showing the proportion of cells expressing TUJ1, MAP2, GFAP, and/or S100. DMEM+10% FBS were used to culture a wide variety of cell types. Dissociated hiNSCs grown in this media for 8 days are still ~90% positive for neuronal marker TUJ1. FIG. 7B demonstrates that provided hiNSCs can be co-cultured with other differentiated cell types while still maintaining neuron-specific expression. C2C12, a murine myoblast cell line, was differentiated and co-cultured with hiNSCs for 4 days. Interestingly, the hiNSCs remained TUJ1-positive even in co-culture with differentiating skeletal muscle cells. Furthermore, these co-cultures exhibited positive alpha-bungarotoxin (α-BTX) immunostaining, indicative of the presence of nicotinic acetylcholine receptors (AChRs) found in neuromuscular junctions, as well as ISLET 1/2 (transcription factor that promotes motor neuron differentiation) and 4E2 (marker of Schwann cell protein found in regenerating nerves at the site of neuromuscular junctions). FIG. 7C shows that, in some embodiments, provided hiNSCs can successfully be used in 3D brain donut models. This model consists of a silk sponge cut into the shape of a "donut", which is coated with laminin. Cells are seeded into this outer ring and allowed to attach. Once attached, a collagen gel is added to the center of the donut, which allows for neurite growth and extension. FIG. 7D shows an exemplary photograph of calcein staining of the donuts in FIG. 7C 24 hours-post seeding. FIG. 7E shows an exemplary image of TUJ1 immunostaining showing neurite extensions into the collagen gel in the 3 week 3D brain cultures in FIG. 7C. FIG. 7F shows a representative snapshot from a video of live calcium signaling in 3D brain cultures.

FIG. 10A shows expression of the endoderm marker FoxA2 as compared to GAPDH, and FIG. 10B shows expression of the mesoderm marker Brachyury as compared to GAPDH.

FIG. 13A shows exemplary immunostaining of 8 day cultures with different concentrations of retinoic acid (RA), GFAP (glia) and DAPI. FIG. 13B shows that in some embodiments, increasing concentrations of retinoic acid (RA) to basal media results in an increase in glial marker expression (GFAP), suggesting that other factors can be identified to generate other specific subtypes of neurons and glia. Scale bars, 100 μm.

FIG. 14A shows frontal sections through the spinal cord demonstrate the presence of human cells as indicated by human nuclear antigen (HUNU) immunostaining, which co-localizes exclusively with Nestin (a neural stem cell marker). FIG. 14B shows a magnified version of the image of FIG. 14A. The scale bars for both panels are 100 μm, and the arrowheads point to cells that co-express HUNU and Nestin).

FIG. 16A shows exemplary immunostaining of hiNSCs after culture with sonic hedgehog (Shh), RA or Shh and RA added to Neurobasal media. An increase in staining of HB9 was observed after one week in culture. TUJI; HB9; DAPI. FIG. 16B shows exemplary immunostaining of hiNSCs after culture with fibroblast growth factor 8 (FGF8), sonic hedgehog (Shh), or FGF8 and Shh added to Neurobasal media. An increase in staining of tyrosine hydroxylase (TH, a marker of dopaminergic neurons) was observed after one week in culture. TUJI; TH; DAPI. Scale bars, 100 μm.

FIGS. 17A and 17B shows that hiNSCs retain proliferative (A) and neurogenic differentiation capacity (B) upon being frozen, thawed and passaged multiple times (here 9 or 25). hiNSC lines were frozen as colonies at passage 3 (P3) and subsequently thawed and expanded on MEF feeder layers for multiple passages and analyzed for Ki67 expression (FIG. 17A). To encourage differentiation, hiNSC colonies were enzymatically dissociated and subcultured on gelatin substrate for 4 days and assayed for TUJI expression (FIG. 17B). Data reflected in graphs of 17A and 17B represent means±SD of 3 independent experiments. FIGS. 17C-17G show that hiNSCs in long term culture, here 25 passages, do not appear to spontaneously induce expression of pluripotency marker OCT4 or germ layer markers. hiNSC lines were cultured in vitro on gelatin (in Knockout DMEM, 20% xeno-free serum replacement, 1% Glutamax, 1% antibiotic-antimycotic, and 0.1 mM—mercaptoethanol, media which could allow for the growth of any potential pluripotent cells resident in this population) for 16 weeks then assayed for neuronal marker TUJI (FIG. 17C), pluripotent marker OCT4 (FIG. 17D), endodermal marker SOX17 (FIG. 17E), mesodermal marker BRACHYURY (FIG. 17F) and ectodermal marker OTX2 (FIG. 17G). Only neuronal marker expression was detectable after this extended period of time in culture (scale bar, 100 μm).

DEFINITIONS

Figure 1:
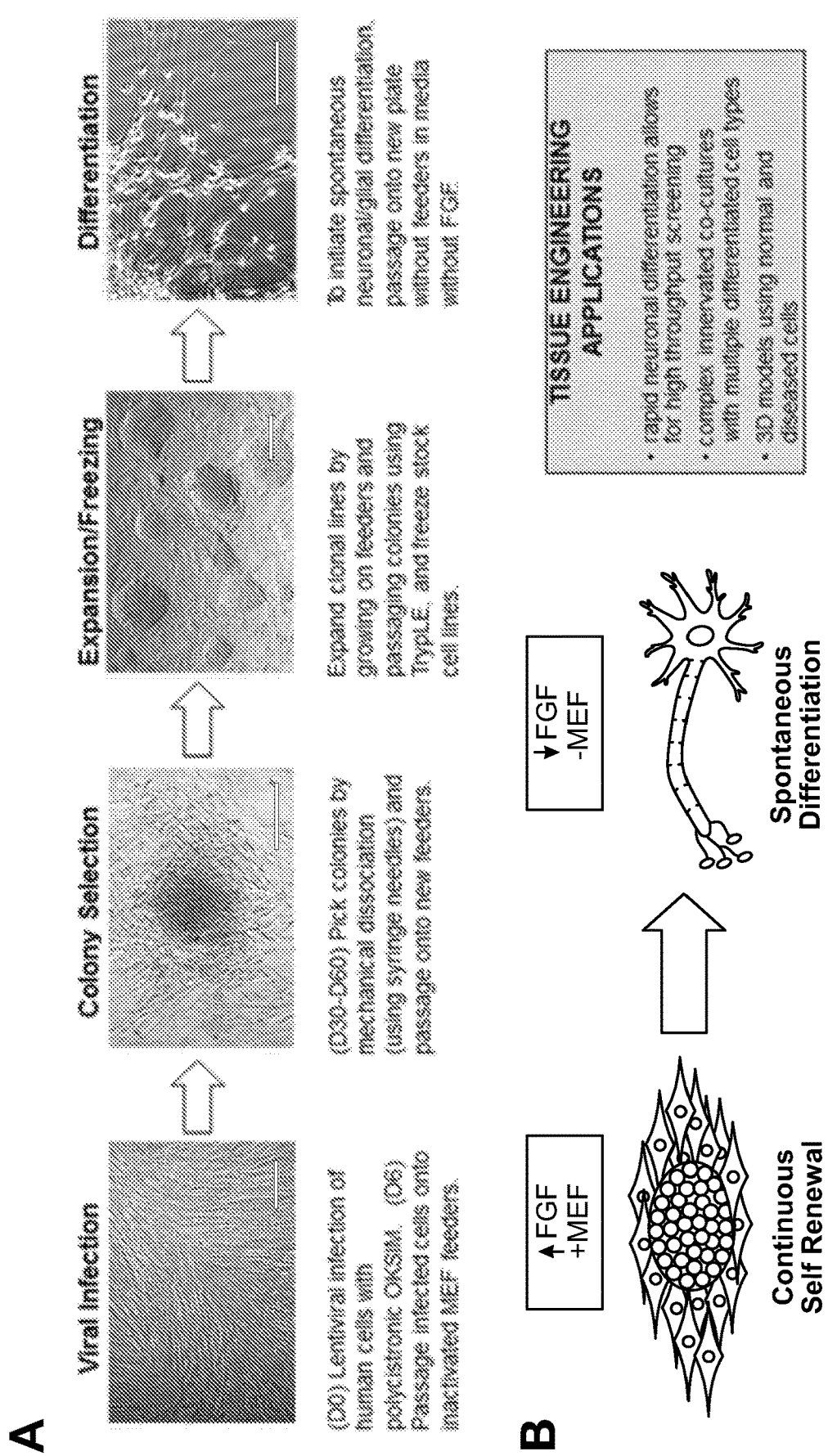
FIGS. 1A and 1B show exemplary methods of reprogramming human cells into induced neural stem cells (hiNSCs).

As used in this application, the terms "about" and "approximately" are used as equivalents. In addition, the terms "human induced neural progenitor", "hiNP", "human induced neural stem cell", and "hiNSC" are also used interchangeably. Any citations to publications, patents, or patent applications herein are incorporated by reference in their entirety. Any numerals used in this application with or without about/approximately are meant to cover any normal fluctuations appreciated by one of ordinary skill in the relevant art.

Adult: As used herein, the term "adult" refers to a human eighteen years of age or older. In some embodiments, a human adult has a weight within the range of about 90 pounds to about 250 pounds.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide, genetic signature, metabolite, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biomarker: As used herein, the term "biomarker", consistent with its use in the art, refers to a to an entity whose presence, level, or form, correlates with a particular biological event or state of interest, so that it is considered to be a "marker" of that event or state. To give but a few examples, in some embodiments, a biomarker may be or comprises a marker for a particular disease state, or for a particular stage of cellular development and/or cellular lineage. In some embodiments, a biomarker may be or comprise a marker for a particular disease or therapeutic outcome, or likelihood thereof. Thus, in some embodiments, a biomarker is diagnostic of a relevant biological event or state of interest. A biomarker may be an entity of any chemical class. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells, e.g., is secreted or is otherwise generated or present outside of cells, e.g., in a body fluid such as blood, urine, tears, saliva, cerebrospinal fluid, media, etc.

Comparable: As used herein, the term "comparable" refers to two or more agents, entities, situations, sets of conditions, etc., that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Expression: As used herein, the term "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In some embodiments expression is transient expression.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Neonatal: As used herein the term "neonatal" refers to a human between birth and 18 years of age. Body weight can vary widely across ages and specific neonates, with a typical range being 8 pounds to 150 pounds.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic. Those of ordinary skill in the art, reading the present disclosure, will appreciate that certain small molecule compounds described herein may be provided and/or utilized in any of a variety of forms such as, for example, salt forms, protected forms, pro-drug forms, ester forms, isomeric forms (e.g., optical and/or structural isomers), isotopic forms, etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

DETAILED DESCRIPTION OF CERTAIN EMBODIMENTS

As described herein, the present invention provides a variety of new and powerful methods with which to generate human induced neural stem cells which may be passaged indefinitely, subjected to freeze-thaw conditions repeatedly, and which maintain their ability to eventually differentiate into neurons or glia, even in a mixed culture environment.

Previous Cellular Reprogramming Efforts to Produce Neuronal Cells

The discovery of induced pluripotent stem cell (iPSC) technology revolutionized the field of stem cell biology. Introduction of the four reprogramming factors Oct4, Sox2, Klf4 and c-Myc into somatic cells under defined conditions results in iPSCs, which, like human embryonic stem cells (hESCs), have the capacity to subsequently differentiate into cell types of all three germ layers. A number of protocols have been described for the differentiation of iPSCs into various neuronal phenotypes, including those for various patient-specific disease models such as Parkinson's and Alzheimer's disease. However, these protocols are often very time consuming, require multiple complicated intermediate steps including the formation of neurospheres (unlike the methods provide herein), and result in a large variability in neuronal differentiation capacity. Furthermore, a recent report suggested that these iPSC-derived NSCs can spontaneously regain pluripotency (Choi et al. 2014), suggesting that this type of NSC may not be suitable for clinical applications.

In recent years, various groups have established methods to directly reprogram induced neurons (iNs). For example, Pang et. al. demonstrated that the forced expression of Brn2, Ascl1, Mytl1, NeuroD1 converted fetal and postnatal human fibroblasts into induced neurons capable of generating action potentials (Pang et al. 2011). Pereira et. al. used a similar approach to yield human induced neurons (hiNs) capable of surviving transplantation into the adult rat brain (Pereira et al. 2014). This method of direct reprogramming into induced neurons circumvents some of the issues associated with the generation of iPSCs followed by subsequent neuronal differentiation, including teratoma formation resulting from a pluripotent intermediate and the extended time frame required for this differentiation process, however hiNs have their own challenges. Because neurons are terminally differentiated, directly reprogrammed hiNs are also unable to proliferate, thereby posing issues with respect to generating a sufficient supply of cells for various applications.

Human Induced Neural Stem Cells (hiNSCs)

Unlike previous methods, the present invention provides, inter alia, methods for generating hiNSCs that have previously unattainable properties. The present invention is based, in part, on the surprising discovery that human induced neural stem cells (hiNSCs) may be created from any human somatic cell (not only those of ectodermal origin) and that the hiNSCs resulting from provided methods are able to be passaged indefinitely without losing proliferative and/or differentiation capacities (e.g., a substantially undiminished capacity for self-renewal). In other words, according to various embodiments, cells produced by provided methods may be clonally reproduced indefinitely without suffering from the cell death or spontaneous differentiation observed in cells produced by previous methods.

In addition, according to various embodiments, provided hiNSCs produced by provided methods are able to be differentiated into neurons and/or glia without the need to form an intermediate neurosphere (which are known to be non-adherent), a common and cumbersome step required in previous methods. For the purposes of tissue engineering, avoiding neurosphere formation is ideal because once cells have been equilibrated to low adhesion conditions, the transition to adherent monolayer or 3D culture is sometimes difficult. Furthermore, the center part of neurospheres can often become necrotic.

Further, in some embodiments, the present invention provides methods to guide differentiation, for example, of a population of hiNSCs, into one or more neuronal subtypes, including, e.g. motor neurons and dopaminergic neurons. In some embodiments, guided differentiation into neuronal subtypes may occur over a period of time of 1 week or less. In some embodiments, guided differentiation into neuronal subtypes may occur over a period of time of 2 weeks or less. In some embodiments, guided differentiation into neuronal subtypes may occur over a period of about seven to eight days.

In some embodiments, provided methods allow for guided differentiation of a majority of, for example, hiNSCs, into a primarily motor neuron culture (e.g., greater than 50%, 60%, 70%, 80%, 90% of the cells in culture become motor neurons). In some embodiments, such methods include a step of associating a population of human induced neural stem cells with culture media comprising 500 ng/ml sonic hedgehog (Shh) and 10 uM retinoic acid (RA). In some embodiments, the culture media is or comprises BL27-based media.

In some embodiments, provided methods allow for guided differentiation of a majority of, for example, hiNSCs, into a primarily dopaminergic neuron culture (e.g., greater than 50%, 60%, 70%, 80%, 90% of the cells in culture become dopaminergic neurons). In some embodiments, such methods include a step of associating a population of human induced neural stem cells with culture media comprising 500 ng/ml FGF8. In some embodiments, the culture media is or comprises BL27-based media.

In some embodiments, provided methods allow for guided differentiation of a majority of, for example, hiNSCs, into a primarily glial culture (e.g., greater than 50%, 60%, 70%, 80%, 90% of the cells in culture become glia). In some embodiments, such methods include a step of associating a population of human induced neural stem cells with culture media comprising 100 μM retinoic acid (RA). In some embodiments, the culture media is or comprises DMEM/FBS-based media.

In some embodiments, the present invention provides methods including the steps of providing one or more human somatic cells, causing transient increased expression of OCT4, KLF4, SOX2, and cMYC in the somatic cells forming modified somatic cells, providing a plurality of inactivated embryonic fibroblasts, associating the modified somatic cells with the inactivated embryonic fibroblasts in a culture media comprising 20% KO DMEM xeno-free serum replacement and at least 15 ng/ml recombinant bFGF to form human induced neural stem cells. In some embodiments, the inactivated embryonic fibroblasts are associated with the modified somatic cells in a culture media comprising 20% KO DMEM xeno-free serum replacement and at least 20 ng/ml recombinant bFGF.

Somatic Cells

Provided methods provide powerful new ways to modify any human somatic cell, according to various embodiments. A somatic cell is defined as any biological cell forming the body of a multicellular organism (e.g., a human), other than a gamete, germ cell, gametocyte or undifferentiated stem cell. It is contemplated that any somatic cell may be used according to some embodiments. Non-limiting examples of somatic cells include, but are not limited to fibroblasts, adipocytes, dermal cells, epidermal cells, muscle cells, and bone cells. In some embodiments, the human somatic cells are adult human somatic cells. In some embodiments, the human somatic cells are neonatal human somatic cells.

Transient Expression

According to various embodiments, any of a variety of methods may be used to cause increased transient expression of OCT4, KLF4, SOX2, and cMYC in the somatic cells. Exemplary methods of causing the transient expression of one or more of OCT4, KLF4, SOX2, and cMYC in human cells may be found, inter alia, in Somers et al. 2012 (Stem Cells, 28(10): 1728-1740), the disclosure of which is hereby incorporated in its entirety. In some embodiments, the transient increased expression is caused by a vector (e.g., a viral vector). In some embodiments, the vector is a polycistronic vector. In some embodiments, the polycistronic vector is a lentivirus. In some embodiments, the transient expression is caused by at least one of a small molecule and a nucleic acid (e.g., an RNA).

Inactivated Embryonic Fibroblasts

In accordance with various embodiments, one or more populations of inactivated embryonic fibroblasts may be used. It is specifically contemplated that any embryonic fibroblasts may be suitable for use in some embodiments. As used herein, the term "inactivated fibroblast" means a mitotically inactivated fibroblast. Methods of preparing inactivated fibroblasts are well known and it is specifically contemplated that any such method may be used in accordance with various embodiments. Exemplary methods of preparing inactivated fibroblasts may be found, inter alia, in Current Protocols in Molecular Biology (specifically Conner, D. A. 2001. Mouse Embryo Fibroblast (MEF) Feeder Cell Preparation. Current Protocols in Molecular Biology. 51:23.2:23.2.1-23.2.7), the disclosure of which is hereby incorporated in its entirety. In some embodiments, inactivated human embryonic fibroblasts are used. In some embodiments, inactivated mouse embryonic fibroblasts are used. Inactivated embryonic fibroblasts may also be referred to herein as "feeder cells", for example, inactivated mouse embryonic fibroblasts may be referred to as "mouse embryonic feeder cells" or "MEFs".

According to various embodiments, any method of inactivating embryonic fibroblasts may be used in an application-appropriate manner. In some embodiments, the mouse embryonic fibroblasts are inactivated via one or more of a DNA crosslinking agent, for example, mitomycin C treatment, and irradiation, for example, gamma irradiation.

Xeno-Free Media

According to several embodiments, xeno-free media (i.e., media containing no non-human substances) may be used to maintain provided human induced neural stem cells in an undifferentiated state. In some embodiments, the xeno-free media may be or comprise serum-free media. In some embodiments, the xeno-free media may comprise a serum replacement, such as a 20% xeno-free KO Dulbecco's Modified Eagle Medium (DMEM) serum replacement. In some embodiments, xeno-free media may be or comprise CTS™ KNOCKOUT™ SR XenoFree Media (GIBCO®). In some embodiments, the use of xeno-free media may be combined with a high level of bFGF in the media, for example 15 ng/ml or more (e.g., 20 ng/ml, 25 ng/ml, 30 ng/ml, 35 ng/ml, 40 ng/ml, 45 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml or more).

Without wishing to be held to a particular theory, it is possible that the feeder cells, for example MEF feeder cells, are helping to maintain continuous self-renewal of hiNSCs, while the xeno-free serum replacement, which lacks the ability to maintain pluripotency of cells, and the high levels of FGF work in combination to promote the neural stem cell fate. In some embodiments, provided human induced neural stem cells are not exposed to neuron-specific media, for example, neurobasal media. In some embodiments, provided human induced neural stem cells are not exposed to BDNF. In some embodiments, provided human induced neural stem cells are not exposed to GDNF.

Basic Fibroblast Growth Factor (bFGF)

According to various embodiments, the modified somatic cells form human induced neural stem cells upon association with inactivated embryonic fibroblasts in a high bFGF environment. In some embodiments, a high bFGF environment may be defined as at least 15 ng/ml bFGF present in the culture media (e.g., 16 ng/ml, 17 ng/ml, 18 ng/ml, 19 ng/ml). In some embodiments, a high bFGF environment may be defined as at least 20 ng/ml bFGF present in the culture media (e.g., at least 25 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml or more). In some embodiments, a high bFGF environment may be defined as between about 15 ng/ml and 500 ng/ml bFGF present in the culture media (e.g., 20 ng/ml to 500 ng/ml).

In accordance with various embodiments, provided human induced neural stem cells are encouraged to differentiate, in whole or in part, through removal from feeder cells and exposure to a low bFGF environment. In some embodiments, a low bFGF environment may be defined as less than 15 ng/ml bFGF present in the culture media (e.g., less than 14 ng/ml, 13 ng/ml, 12 ng/ml, or 11 ng/ml). In some embodiments, a low bFGF environment may be defined as less than 10 ng/ml bFGF present in the culture media (e.g., less than 9 ng/ml, 8 ng/ml, 7 ng/ml, or 6 ng/ml). In some embodiments, a low bFGF environment may be defined as less than 5 ng/ml bFGF present in the culture media (e.g., less than 4 ng/ml, 3 ng/ml, 2 ng/ml, or 1 ng/ml). In some embodiments, a low bFGF environment may be defined as substantially no bFGF present in the culture media. In some embodiments, a low bFGF environment may be defined as between 14 ng/ml and substantially no bFGF present in the culture media.

Proliferative and Differentiation Capacity

In some embodiments, provided methods allow for previously unattainable levels of self-renewal. In some embodiments, provided human induced neural stem cells are able to be maintained for at least one year (e.g., under growth conditions) prior to dissociation. In some embodiments, provided human induced neural stem cells are able to be maintained for at least two years (e.g., under growth conditions) prior to dissociation. In some embodiments, provided human induced neural stem cells may be passaged at least 15 times (e.g., at least 25 times) while associated with the inactivated mouse embryonic fibroblasts without substantial differentiation occurring.

In some embodiments, provided methods allow for substantial periods of growth, for example, more than 8 passages (e.g., 10, 15, 20, 25, 30, 35, 40, 45, 50, 55, 60, 65, 70, 75, 80, 85, 90, 95, 200 passages or more), without substantial loss of at least one of proliferation capacity and/or differentiation capacity. In some embodiments, proliferation capacity is measured via at least one of Ki67 immunostaining, a BrdU incorporation assay, a Resazurin or other redox-based assay, and a growth curve/measure of doubling time. In some embodiments, differentiation capacity is measured via at least one immunostaining assay, for example, Tuj1 immunostaining. In some embodiments, differentiation capacity is measured via at least one fluorescence-based assay, for example, a luciferase-based assay (e.g., an assay such as that described in Hughes, D., et al (2012) Characterization of early phenotypic changes in differentiating NCCIT cells using multiplexed luciferase reporters and immunofluorescence imaging. Poster #633.25. Presented Tuesday, Oct. 16, 2012. Society for Neuroscience Annual Meeting. New Orleans, La.). In some embodiments, both proliferation capacity and differentiation capacity may be measured using the same assay or kit.

In some embodiments, provided methods allow for freezing and thawing of provided human induced neural stem cells without substantial loss of at least one of proliferation capacity and differentiation capacity. In some embodiments, provided human induced neural stem cells are able to be frozen and thawed at least once and maintain at least a 90% proliferation capacity. In some embodiments, provided human induced neural stem cells are able to be frozen and thawed at least five times and maintain at least a 90% proliferation capacity.

According to various embodiments, proliferation capacity may be measured via any method known in the art. In some embodiments, proliferation capacity is measured via at least one of Ki67 immunostaining, a BrdU incorporation assay, and a growth curve/measure of doubling time. In some embodiments, provided human induced neural stem cells are able to be frozen and thawed at least once with substantially no loss in differentiation capacity. In some embodiments, provided human induced neural stem cells are able to be frozen and thawed at least five times (e.g., at least 10, 15, 20, 25, 30, 35, 40, 45, 50 or more times) with substantially no loss in differentiation capacity. In some embodiments, differentiation capacity is measured via at least one immunostaining assay, for example, Tuj1 immunostaining. In some embodiments, differentiation capacity is measured via at least one fluorescence-based assay, for example, a luciferase-based assay as described above. In some embodiments, both proliferation capacity and differentiation capacity may be measured using the same assay or kit.

In some embodiments, once removed from feeder cells, dissociated from colonies into single cells, and subsequently cultured in media with reduced levels of FGF, hiNSCs may differentiate into neuronal and glial phenotypes. Their high proliferation rate allows for a generation of large quantities of cells often required for tissue engineering applications. Furthermore, their rapid and robust capacity for neuronal differentiation makes them ideal for high throughput assays as well as multicellular co-culture models.

In some embodiments, hiNSC cells that have spontaneously differentiated into cells that comprise neurons and/or glia may be further guided, using provided methods, to differentiate into specific neuronal and/or glial subtypes. In some embodiments, guided differentiation is accomplished by adding one or more exogenous material (e.g., growth factors) to a culture containing hiNSCs that have differentiated into cells comprising neurons.

Fibroblast Growth Factor 8 (FGF8)

According to various embodiments, dissociated human induced neural stem cells can be guided to differentiate into specific neuronal subtypes. In some embodiments, guided differentiation occurs through addition of FGF8 to culture media. In some embodiments, FGF8 may be used at a final culture concentration of at least 10 µM FGF8 (e.g., 10 µM, 15 µM, 20 µM, 25 µM, or more). In some embodiments, FGF8 may be used at final culture concentrations of at least 50 uM FGF8 (e.g., at least 60 µM, 65 µM, 70 µM, 75 µM, 80 µM, 85 µM, 90 µM, 95 µM, 100 µM or more). In some embodiments, FGF8 may be added to culture media at final concentrations of between about 10 µM and 500 µM FGF8 present in the culture media (e.g., 10 µM to 400 µM, 10 µM to 300 µM, 10 µM to 200 µM, 10 µM to 100 µM). In some embodiments, addition of FGF8 to hiNSC-derived neurons results in increased proportion of TH-positive cells, suggesting guidance towards a dopaminergic neuron phenotype.

Sonic Hedgehog (Shh)

According to various embodiments, dissociated human induced neural stem cells can be guided to differentiate into specific neuronal subtypes. In some embodiments, guided differentiation occurs through adding Shh to culture media. In some embodiments, Shh may be used at a final culture concentration of at least 10 µM Shh (e.g., 10 µM, 15 µM, 20 µM, 25 µM, or more). In some embodiments, Shh may be used at final culture concentrations of at least 50 µM (e.g., at least 60 µM, 65 µM, 70 µM, 75 µM, 80 µM, 85 µM, 90 µM, 95 µM, 100 µM or more). In some embodiments, Shh may be added to culture media at final concentrations of between about 10 µM and 500 µM Shh present in the culture media (e.g., 10 µM to 400 µM, 10 µM to 300 µM, 10 µM to 200 µM, 10 µM to 100 µM). In some embodiments, addition of Shh to cultures of hiNSC-derived neurons results in increased proportion of HB9-positive cells, as compared to a population of hiNSC-derived neurons not receiving Shh, suggesting guidance towards a motor neuron phenotype. In some embodiments, addition of Shh to cultures of hiNSC-derived neurons results in increased proportion of TH-positive cells, suggesting guidance towards a dopaminergic neuron phenotype.

Retinoic Acid (RA)

According to various embodiments, dissociated human induced neural stem cells can be guided to differentiate into specific neuronal subtypes. In some embodiments, guided differentiation occurs through adding RA to culture media. In some embodiments, RA may be used at a final culture concentration of at least 10 µM RA (e.g., 10 µM, 15 µM, 20 µM, 25 µM, or more). In some embodiments, RA may be used at final culture concentrations of at least 50 µM RA (e.g., at least 60 µM, 65 µM, 70 µM, 75 µM, 80 µM, 85 µM, 90 µM, 95 µM, 100 µM or more). In some embodiments, RA may be added to culture media at final concentrations of between about 10 µM and 500 µM RA present in the culture media (e.g., 10 µM to 400 µM, 10 µM to 300 µM, 10 µM to 200 µM, 10 µM to 100 µM). In some embodiments, addition of RA to hiNSC-derived neurons results in increased proportion of HB9-positive cells, suggesting guidance towards a motor neuron phenotype.

Combinations of FGF8, Shh and/or RA

In some embodiments, FGF8, Shh and/or RA are added to the same cultures of hiNSCs. In some embodiments, FGF8, Shh and/or RA are added to different cultures hiNSCs. In some embodiments, the addition of FGF8, Shh, and/or RA results in increased numbers of TH-positive cells (e.g., dopaminergic neurons). In some embodiments, the addition of at least two of FGF8, Shh, and RA results in greater numbers of HB9-positive cells (e.g., motor neurons) than the addition of FGF8, Shh, or RA alone. In some embodiments, the addition of FGF8 alone results in greater numbers of HB9-positive cells than the addition of Shh or RA alone or the combination of Shh, FGF8, and/or RA.

EXAMPLES

Example 1: Generation of Expandable Human Induced Neural Stem Cells (hiNSCs)

The present example demonstrates an exemplary method to generate certain hiNSCs. The cells provided in this example expressed neural stem cell markers, were able to be cultured while maintaining an undifferentiated state, and showed positive proliferation.

Unless otherwise specified, the materials and methods used in this example were as follows:

Polycistronic Lentivirus Production for Reprogramming

To generate pluripotent stem cells from somatic cells, a vector that expresses the reprogramming factors OCT4, KLF4, SOX2, and cMYC in a polycistronic lentivirus was used (Addgene #24603). This polycistronic lentivirus also contains a LoxP site that allows for transgene removal upon addition of Cre-recombinase. HEK293 cells were used for packaging the virus. These cells were grown in DMEM, 10% fetal bovine serum (FBS), and 1% antibiotic-antimycotic. The cells were co-transfected with the lentivirus construct, and psPAX and pMD2.G packaging vectors (Addgene #12260 and 12259) using Fugene (Roche). Culture medium was harvested 24- and 48-hrs post-transfection. Viral particles were concentrated using Lenti-X concentrator (Clontech), then centrifuged at 3000 rpm. Concentrated viruses were titered and subsequently stored at −80° C. until further use.

Generation of hiNSCs

Human neonatal foreskin fibroblasts (HFFs) or adult human adipose-derived stem cells (hASCs) isolated as previously described (Abbott, Raja et al. 2015) were used to generate hiNSCs. Briefly, HFFs or hASCs were plated at a concentration of $10^5$ cells in one gelatin-coated well of a 6-well plate, and cultured in fibroblast media (DMEM, 10% FBS, and 1% antibiotic-antimycotic). Concentrated virus was used to infect the cells in fibroblast medium with polybrene (Millipore) at an MOI=1-2. The next day, media was changed to fresh fibroblast medium. The following day, media was changed to hiNSC media: KO DMEM supplemented with 20% KO xeno-free serum replacement, 20 ng/mL recombinant bFGF, 1% Glutamax, 1% antibiotic-antimycotic, and 0.1 mM β-mercaptoethanol (Invitrogen), which also contained 1% KO growth factor cocktail (GFC) (Invitrogen). Four days later, cells were trypsinized and re-plated on mouse embryonic fibroblast (MEF) feeder layers previously inactivated by mitomycin C. hiNSC media (without KO-GFC) was subsequently changed every 1-2 days. Around day 30 or later, colonies with a domed morphology somewhat similar to hESC lines were mechanically picked and passaged onto freshly mitotically inactivated MEFs. Each colony was used to generate one hiNSC line, and these cell lines were expanded as colonies on MEF feeder layers. For further expansion, hiNSCs were enzymatically passaged as colonies using TrypLE (Invitrogen) onto new MEF feeders for multiple passages, and subsequently frozen to make stocks. All hiNSC clonal lines were assayed for pluripotency and neural stem cell markers by RT-PCR and immunofluorescence.

Pluripotent Stem Cell and Neural Stem Cell Culture

The H1 human ES cell line (Wicell) was grown on mouse embryonic fibroblast feeder layers inactivated by mitomycin C treatment in Knockout (KO) DMEM supplemented with 20% KO serum replacement (not xeno-free), 10 ng/mL recombinant bFGF, 1% Glutamax, 1% antibiotic-antimycotic, and 0.1 mM β-mercaptoethanol (Invitrogen). Colonies were expanded by enzymatically passaging using a trypsin-like enzyme (TrypLE; Invitrogen). Commercially available cell lines were cultured as controls for human neural stem cells. H9-NSCs (Invitrogen) are neural stem cells derived from H9 hESC lines. Human neural progenitors (hNPs, ReNcell) are an immortalized human neural progenitor cell line derived from human fetal brain tissue. Both H9-NSCs and hNPs were cultured using hiNSC media, on gelatin and laminin (Roche) coated plates, respectively.

Differentiation into Neuronal and Glial Phenotypes

To encourage spontaneous differentiation, hiNSC colonies were enzymatically removed from MEF feeder layers using TrypLE (Invitrogen), then dissociated as much as possible by manually pipetting. This cell suspension was sometimes further separated into a single cell suspension using a 40-70 μM cell strainer to remove larger clumps. Dissociated hiNSCs were plated and cultured on multiple substrates including CELLstart (Invitrogen), laminin (Roche) or gelatin in hiNSC basal media without bFGF or in neurobasal media supplemented with 2% B27 (Invitrogen), 1% Glutamax, and 1% antibiotic-antimycotic. hiNSC cells began to show differentiation into BIII-tubulin (TUJ1)-positive immature neurons with visible neurite extensions in as little as 4 days. After two weeks in basal media, hiNSC cells spontaneously differentiated into more mature neuronal and glial subtypes. Adding various amounts of retinoic acid (10-100 μM) caused cells to differentiate into more mature neuronal phenotypes in a shorter amount of time (~8 days). Dissociated hiNSCs cultured in generic cell culture media used for culturing a wide variety of cell types, DMEM supplemented with 10% FBS and 1% antibiotic-antimycotic, also resulted in mostly TUJ1+ neurons after one week in culture. For guided differentiation, Shh (500 ng/ml, Peprotech), FGF8 (500 ng/ml, Peprotech), and RA (R&D) at concentrations between 10-100 μM were used to facilitate neuronal and glial differentiation within shorter culture periods (~7-8 days). For differentiation studies in undefined media, DMEM supplemented with 10% FBS and 1% antibiotic-antimycotic was used.

Co-Culture of hiNSCs with Skeletal Muscle Cells

C2C12 murine myoblast cell line (ATCC) was cultured in DMEM+10% FBS (Invitrogen). For skeletal muscle differentiation, cells were cultured at high confluence in DMEM+1% FBS to induce myotube formation. hiNSC colonies that had been removed from feeders and subcultured on gelatin for 2 weeks were subsequently trypsinized with TrypLE, then passaged onto differentiating C2C12 cultures. Co-cultures were maintained for 4 days, and fixed for immunofluorescent analysis.

3D Brain Donut Model

Silk donut scaffolds were generated as previously described (Tang-Schomer, White et al. 2014; Chwalek, Tang-Schomer et al. 2015). Briefly, porous salt-leached aqueous silk sponges were generated, and 6 mm discs were cut using biopsy punches, into which 2 mm holes were removed from the center. These donut scaffolds were sterilized and coated with laminin (Roche). Dissociated hiNSCs were seeded into the scaffolds at a density of $1 \times 10^6$ and allowed to adhere overnight. The following day, collagen gels were made using rat tail collagen (Corning) as previously described. 3D brain models were then cultured in neurobasal media supplemented with 2% B27 (Invitrogen), 1% Glutamax, and 1% antibiotic-antimycotic for up to five weeks, with media changes every 1-3 days.

Immunofluorescence

Briefly, cells grown in culture plates, on coverslips, or in 3D silk scaffold cultures were fixed in 4% paraformaldehyde, then washed with 1× phosphate-buffered saline (PBS). Samples were incubated with blocking buffer consisting of PBS containing 10% goat serum and 0.1% triton X-100. Primary antibodies were added to blocking buffer, and incubated with samples overnight at 4° C. The following day, samples were washed several times with PBS, then incubated with a corresponding fluorescently-conjugated secondary antibody in blocking buffer, for 1 hour at room temperature (away from light). Nuclei were counterstained with DAPI (Invitrogen). For immunostaining of tissues from in vivo studies, slides mounted with previously fixed cryo-sectioned tissues were used following a similar protocol. All antibodies used in this study are listed in Supplemental Table 1.

SUPPLEMENTAL TABLE 1

| Host | Antigen | Vendor | Catalog # |
|---|---|---|---|
| Rabbit | OCT4 | Stemgent | 09-0023 |
| Rabbit | SOX2 | Stemgent | 09-0024 |
| Rabbit | NANOG | Stemgent | 09-0020 |
| Mouse | SSEA4 | Stemgent | 09-0006 |
| Mouse | TRA-1-81 | Stemgent | 09-0011 |
| Rabbit | PAX6 | Stemgent | 09-0075 |
| Rabbit | SOX1 | Abcam | ab87775 |
| Rabbit | NESTIN | Sigma | N5413 |
| (APC-conjugated) | CD133 | Miltenyi Biotec | 130-098-829 |
| Rabbit | KI67 | Abcam | ab15580 |
| Rabbit | TUJ1 | Abcam | ab18207 |
| Mouse | TUJ1 | Sigma | T8578 |
| Mouse | GFAP | Sigma | G3893 |
| Rabbit | GFAP | Sigma | G9269 |
| Mouse | TH | Sigma | T1299 |
| Rabbit | SLC32A1/VGAT | Sigma | SAB2700790 |
| Rabbit | VGLUT2 | Sigma | V2514 |
| Rabbit | VGLUT1 | Sigma | V0389 |
| Mouse | GEPHYRIN | Abcam | ab124385 |
| Mouse | PSD95 | Sigma | p246 |
| Rabbit | SYNAPTOPHYSIN | Abcam | ab32594 |
| Rabbit | PAN NAV | Alomone | ASC-003 |
| Rabbit | S100β | Millipore | 04-1054 |
| Rabbit | MBP | Millipore | AB980 |
| Mouse | O4 | Millipore | MAB345 |
| Mouse | HUNU | Millipore | MAB1281 |
| Cy3-conjugated mouse | HUNU | Millipore | MAB4383C3 |
| Mouse | HB9 | DSHB | 81.5C10 |
| Mouse | NF (sensory/motor) | DSHB | E1.9 |
| Rabbit | MAP2 | Sigma | M3696 |
| Rabbit | NEUN | Abcam | ab104225 |
| Rabbit | S100 | Abcam | ab76729 |
| Mouse | MHC | DSHB | MF20 |
| Mouse | ISLET1/2 | DSHB | 39.4D5 |
| Mouse | Schwann cell protein | DSHB | 4E2(3G2) |
| Alexa 647 conjugated | Bungarotoxin | Invitrogen | B-13423 |
| Goat (Alexa 488 conjugated) | Rabbit IgG | Invitrogen | A-11070 |
| Goat (Alexa 594 conjugated) | Rabbit IgG | Invitrogen | A-11072 |
| Goat (Alexa 488 conjugated) | Mouse IgG | Invitrogen | A-11017 |
| Goat (Alexa 594 conjugated) | Mouse IgG | Invitrogen | A-11020 | qRT-PCR

Total RNA was isolated using the RNeasy Mini kit (Qiagen), and cDNA was generated using MLV-reverse transcriptase (Invitrogen, CA) according to the manufacturers' protocols. Quantitative RT-PCR was performed on the iQ5 Real-Time PCR Detection System (BioRad) and normalized against the housekeeping gene GAPDH. All primer sequences are listed in Supplemental Table 2.

SUPPLEMENTAL TABLE 2

Primer sequences used for qRT-PCR.

| Gene | Accession No. | Sequence 1 (5'→3') | Sequence 2 (5'→3') |
|---|---|---|---|
| endo Oct4 | NM_002701.5/ KF880691.1 | AAACCCTGGCACAAACTCCC | GACCAGTGTCCTTTCCTCTG |
| endo Sox2 | NM_003106.3/ JQ231229.1 | CACATGTCCCAGCACTACC | CCATGCTGTTTCTTACTCTCCTC |
| Nanog | NM_024865.3 | TCCTTGCAAATGTCTTCTGCT | CAGGGCTGTCCTGAATAAGC |
| Pax6 | NM_000280.4 | TCCGTTGGAACTGATGGAGT | GTTGGTATCCGGGGACTTC |
| Sox1 | NM_005986.2 | ATTATTTTGCCCGTTTTCCC | TCAAGGAAACACAATCGCTG |
| Sox11 | NM_003108.3 | TTTTCAAGCTCCCTGCAGTT | AGGGACCATTGCAACTTTTG |
| Olig1 | NM_138983.2 | TGGTTACGCTACTTTTGGGG | CCAGTGTTTTGTCGCAGAGA |
| Olig2 | NM_005806.3 | CTGGCGTCCGAGTCCAT | CCTGAGGCTTTTCGGAGC |
| Musashi | NM_002442.3 | GTGAAGGAGTGTCTGGTGATG | GATTGCGCCAGCACTTTATC |
| DCX | NM_000555.3 | TCAGGACCACAGGCAATAAA | AGACCGGGGTTGTCAAAAA |
| PLZF | NM_006006.4 | TTCTCAGCCGCAAACTATCC | ATAACGAGGCTGTGGAGCAG |

SUPPLEMENTAL TABLE 2-continued

Primer sequences used for qRT-PCR.

| Gene | Accession No. | Sequence 1 (5'→3') | Sequence 2 (5'→3') |
|---|---|---|---|
| CD133 | NM_006017.2 | TTTTGGATTCATATGCCTTCTGT | ACCCATTGGCATTCTCTTTG |
| Nestin | NM_006617.1 | AGAACTCCCGGCTGCAAAC | TCTGGGGTCCTAGGGAATTG |
| NCAM | NM_000615.6 | ACTCTCCAACGCTGATCTCC | CAGCCAGCAGATTACAATGC |
| Tuj1 | NM_001197181.1 | GCTCAGGGGCCTTTGGACATCTCTT | TTTTCACACTCCTTCCGCACCACATC |
| polycistronics lentivirus | N/A | GACCACCTCGCCTTACACAT | TTCAGCTCCGTCTCCCATCAT |
| FoxA2 | NM_021784.4 | TACGTGTTCATGCCGTTCAT | CGACTGGAGCAGCTACTATGC |
| Brachyury | NM_003181.3 | CCCTATGCTCATCGGAACAA | CAATTGTCATGGGATTGCAG |

Live Calcium Imaging

Cells plated onto coverslips or on 3D scaffolds were immersed in extracellular solution (NaCl 140 mM, KCl 2.8 mM, CaCl2 2 mM, MgCl2 2 mM, HEPES 10 mM, glucose 10 mM, pH=7.4, adjusted with NaOH). Fluo-4 (Invitrogen) calcium sensitive dye was mixed 1:1 with 20% Pluronic F127 (Invitrogen). Next, Fluo-4 was diluted to a final concentration of 1 µM in the extracellular buffer and pre-warmed to 37° C. The Fluo-4 1 µM solution was applied to cells and incubated at 37° C. for 1 hour. Upon incubation, cells were washed with the extracellular buffer to remove any unreacted dye. Cells were imaged using Olympus MVX10 macroscope (12.6× magnification) and Hamamatsu ORCA-Flash4.0 camera. The images were taken with the following setup: 15 ms exposure, 60 ms frame frequency, 512×512 pixel, 4×4 binning, 1000 frames/minute over 3 minutes at room temperature. Some samples were treated with 200 µM picrotoxin (Sigma-Aldrich) just before imaging. The movie was created using ImageJ software (NIH).

Electrophysiology hiNSCs were grown on poly-L-lysine coated coverslips (Corning) in neurobasal media supplemented with 2% B27 (Invitrogen), 1% Glutamax, and 1% antibiotic-antimycotic for 1-8 weeks. Recordings were performed at 34° C. For whole-cell patch clamp experiments, pipettes contained saline (in mM): 130 K-gluconate, 10 KCl, 0.1 CaCl2, 2 Mg-ATP, 1.1 EGTA, and 10 HEPES, pH 7.4 KOH. Bath saline contained the following (in mM): 140 NaCl, 2.5 KCl, 2.5 CaCl2, 1.2 MgCl2, 10 HEPES, and 11 glucose, pH 7.4 NaOH.

To determine the functionality of GABA receptors, 1-week hiNSC cultures were assessed via known electrophsysiology methods (e.g., voltage ramp) in order to determine the response of neurons resulting from provided hiNSCs both in the presence of muscimol and in its absence.

Specifically, to detect the ability of 8-week cultured hiNSCs to generate action potentials in response to depolarizing current steps, we used prolonged depolarizing currents of 1-second duration per 20 pA step, covering a range from −100 pA to +300 pA. To detect the ability of the cells to generate spontaneous action potentials, we used voltage clamp at 70 mV for 2 min up to 10 min record spontaneous post-synaptic currents. Data were acquired at 10 kHz with PowerLab hardware (ADInstruments) or an Axopatch 200B amplifier (Molecular Devices) and pclamp 10 software (Molecular Devices LLC, Sunnyvale, Calif., USA), and analyzed using Clampfit.

Injection of hiNSCs into Chick Embryos hiNSCs were trypsinized from MEF feeder layers using TrypLE (Invitrogen), and subsequently dissociated by manual pipetting to achieve a single cell suspension. Cells were then fluorescently labeled using DiD (Invitrogen) and washed repeatedly to remove excess dye. Hamburger Hamilton Stage 16 (~55 hours of incubation) chicken embryos (UConn) were used. Briefly, a small window was made in the eggshell to access the embryo, and PBS with antibiotic-antimycotic was added to prevent infection. Fast green dye (1 µl) was added to the cell suspension to visualize the location of the injected cells. Cells entered a pulled borosilicate glass needle by capillary action, and were subsequently injected into the lumen of the developing chick neural tube using a micromanipulator (Parker Picospritzer II). The windowed egg was then sealed using tape. Embryos were harvested and fixed with 4% paraformaldehyde between 1-8 days post-injection for subsequent analysis. Embryos to be cryosectioned were first equilibrated in 15% sucrose-PBS solution, then embedded in OCT. Sections of 10 µM thickness were prepared on slides using a cryostat (Leica).

Microscopy

Brightfield and fluorescent images were obtained using a Keyence BZ-X700 microscope and associated software. Images of 3D fluorescence were taken using confocal or two photon excited fluorescence (TPEF) using a Leica (Wetzlar, Germany) DMIRE2 microscope with a TCS SP2 scanner. Live calcium imaging was performed using Olympus MVX10 macroscope.

Statistical Analysis

All data are expressed as mean±SD. At least 3 independent experiments were performed, with at least 3 independent samples analyzed per experiment. Data demonstrating any statistically significant differences were determined by 1-factor ANOVA with post-hoc Tukey test using the statistics software SYSTAT12 (Systat). A p-value less than 0.05 was considered significant.

Results—Generation of Induced Neural Stem Cells Form Multiple Human Cell Types

Figure 8:
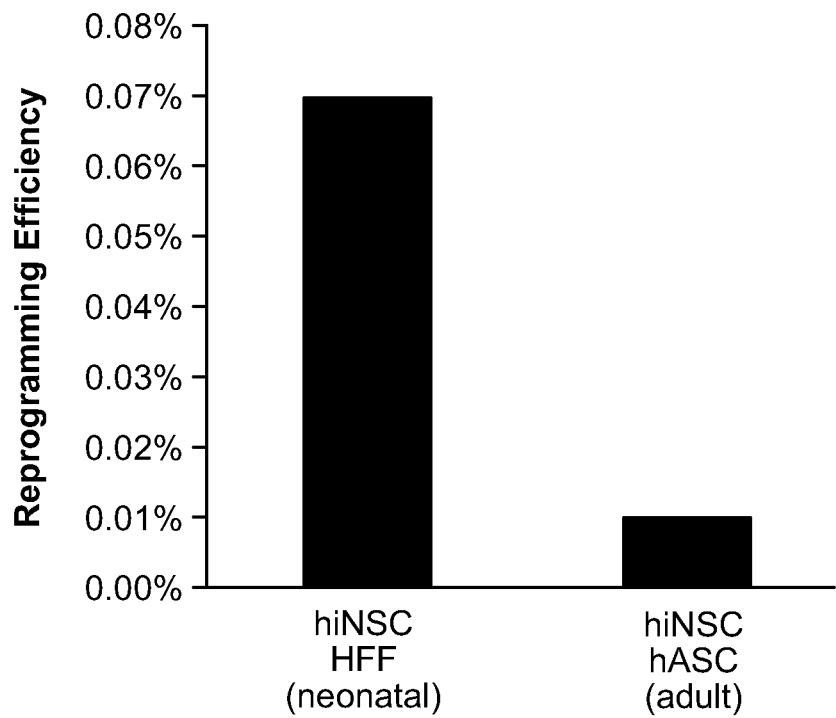
FIG. 8 shows a graph of exemplary reprogramming efficiency of some embodiments of provided methods.

The basic method used to generate human induced neural stem cells (hiNSCs) is depicted in FIG. 1. Briefly, six days after viral infection of human cells with a polycistronic virus expressing the four traditional reprogramming factors (Oct4, Klf4, Sox2, and c-Myc), cells are trypsinized and passaged onto inactivated mouse embryonic feeder (MEF) layers. Colonies begin to emerge with a round, compact morphology (FIG. 1A) after 30-60 days (a longer period of time may be required to reprogram adult cells), these colonies were mechanically picked using syringe needles and transferred to newly inactivated MEF feeders for subsequent expansion, enzymatic passaging and freezing of stocks. Throughout expansion on feeders, the colonies maintain their round, domed morphology. Reprogramming efficiency varied slightly depending on starting cell type (FIG. 8). Once removed from feeders, dissociated into a single cell suspension, and subsequently cultured in media with relatively lower levels of bFGF, hiNSCs spontaneously differentiated into neuronal and glial phenotypes, which can be maintained in long term cultures. The resulting robustness of these hiNSC lines, which includes the ability to rapidly differentiate, the maintenance of neuronal phenotype even in the presence of non-neuronal microenvironments, as well as their ability to grow well in 3D cultures (FIG. 1B), makes this method ideal for a variety of tissue engineering applications.

Figure 2:
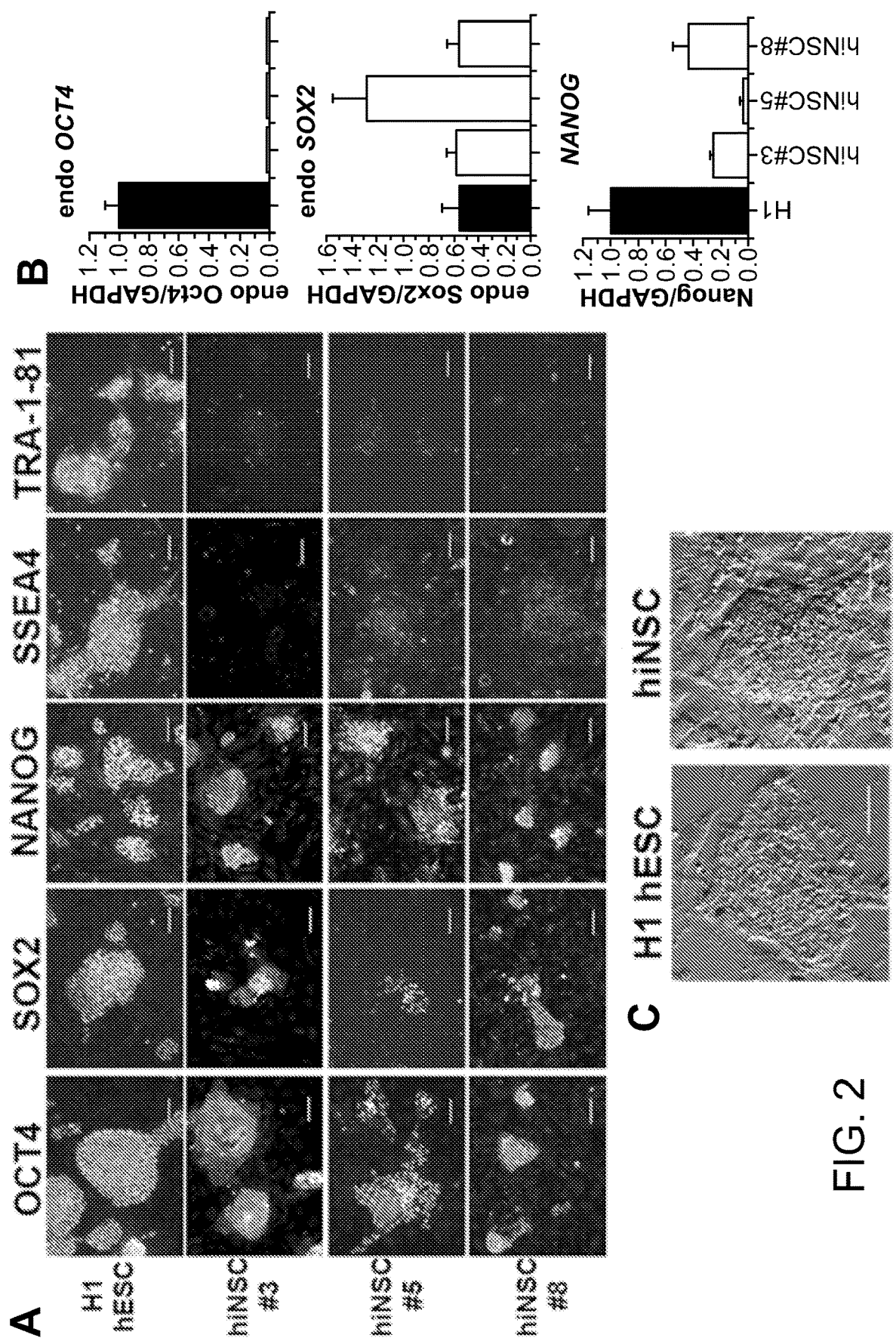
FIGS. 2A-2C show exemplary characteristics of provided hiNSCs, as described herein, hiNSCs may share some but not all characteristics with hESCs.
Figure 9:
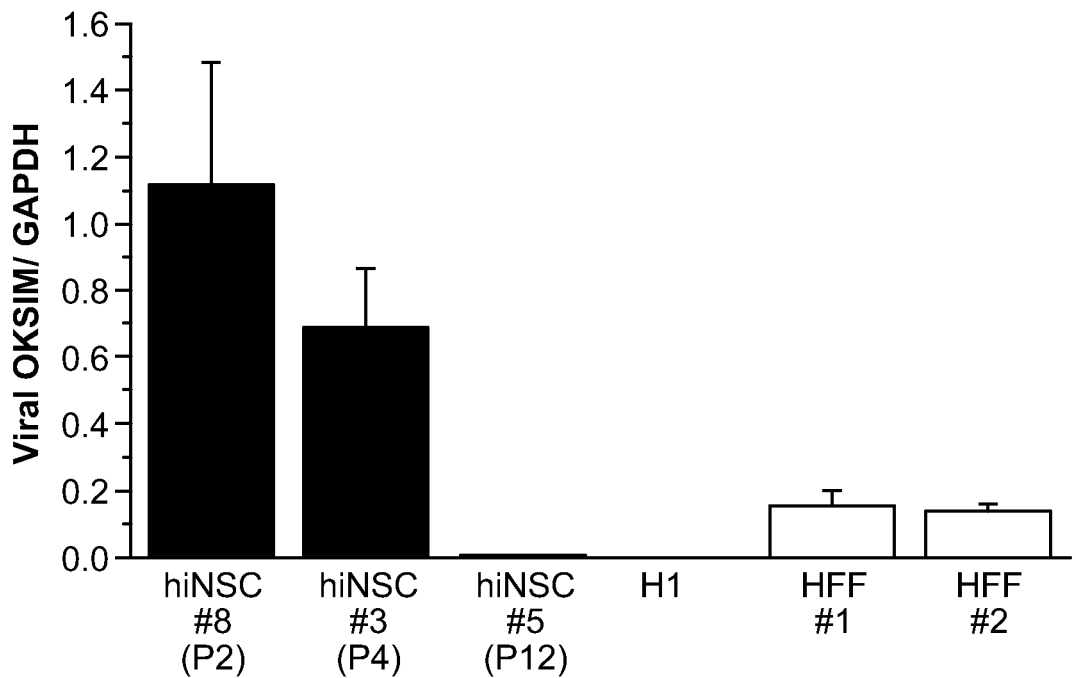
FIG. 9 shows that, according to various provided methods, expression of the exogenous transgenes introduced via polycistronic lentiviral infection is lost upon increased passage of clonal hiNSC lines.
Figure 10:
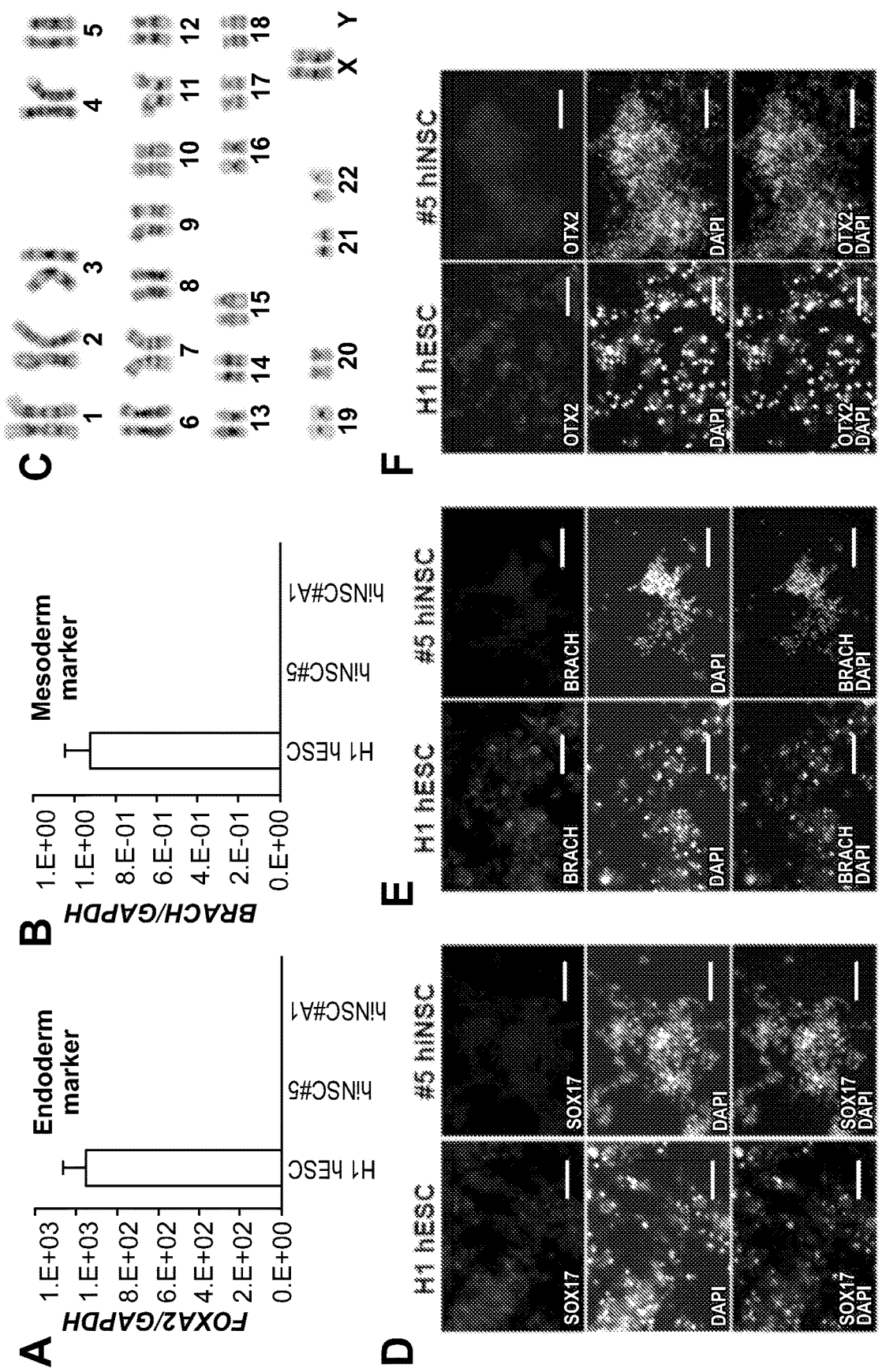
FIGS. 10A and 10B show qRT-PCR analysis of H1 hESC compared to several hiNSC clonal lines and demonstrates that hiNSCs do not express markers of endodermal (FoxA2) or mesodermal (Brachyury) lineages, suggestive of an exclusively ectodermal cell fate.
FIG. 10C shows an exemplary karyotype, confirming that hiNSCs have a normal set of chromosomes.
FIGS. 10D-10F show exemplary immunostaining of hESCs or hiNSCs that were induced to specify endodermal, mesodermal, or ectodermal lineages. hESCs differentiated into SOX17-(FIG. 10D), BRACHYURY- (FIG. 10E) and OTX2- (FIG. 10F) positive cells, whereas hiNSCs did not appear to express markers from endodermal or mesodermal germ layers. Scale bars, 100 µm.

Results—hiNSC Colonies Exhibit Characteristics of Both Embryonic Stem Cells and Neural Stem Cells Reprogramming human cells by this method results in the formation of colonies that exhibit qualities of hESCs as well as hNSCs. These colonies, like hESCs, are positive for Oct4, Sox2 and Nanog, however they do not express typical cell surface markers of pluripotency such as SSEA4 or Tra-1-81 (FIG. 2A), suggesting that these reprogrammed colonies were never actually pluripotent and can therefore not be considered true iPS cells. Interestingly, PCR analysis revealed that while these reprogrammed hiNSC colonies express pluripotent transcription factor Nanog, they also express relatively high levels of endogenous Sox2 expression, but not that of endogenous Oct4 (FIG. 2B), providing further evidence of the lack of a pluripotent state. Sox2 has been shown to be a marker of self-renewing, multipotent NSCs (Graham, Khudyakov et al. 2003; Ellis, Fagan et al. 2004), and its endogenous upregulation is suggestive of a NSC fate. It is also important to note that exogenous transgene expression of the polycistronic virus is lost upon increased passage of the colonies (FIG. 9). While hESCs have the capacity to differentiate to cells of all three germ layers, endoderm, mesoderm and ectoderm, hiNSCs do not express markers of endoderm or mesoderm (FIG. 10), which provides further evidence of their specific ectodermal fate. Furthermore, while both undifferentiated hESC and hiNSC grow in tightly packed colonies with clear margins, their respective morphologies are somewhat distinct (FIG. 2C). In these exemplary embodiments, growing on MEF feeders, hESC colonies appear relatively flat, while hiNSC colonies are typically more dome-like in shape.

Figure 3:
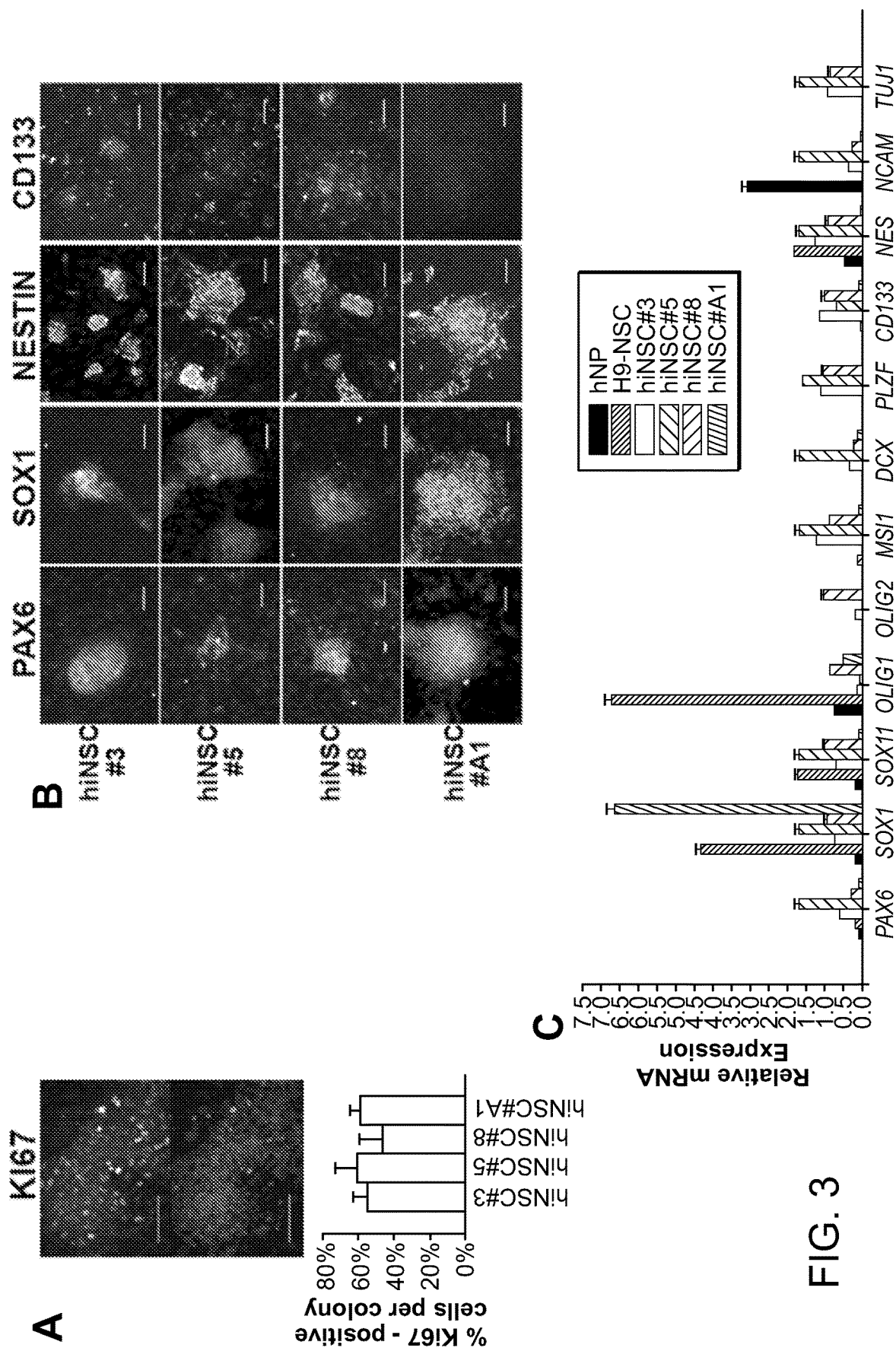
FIG. 3A-3C shows that provided hiNSCs can be self-renewing.

While the hiNSC colonies in this Example share certain similarities with hESC, they also share multiple characteristics with neural stem cells. One accepted criterion of NSCs is the ability to self-renew. These reprogrammed hiNSCs when grown as colonies on MEFs typically show an average between 46-60% Ki67-positive cells for all clonal lines tested. (FIG. 3A). Furthermore, immunostaining results demonstrate that these clonal lines express various markers typical of NSCs including Sox1, Pax6, Nestin and CD133 (FIG. 3B). Compared to various established human neural cell lines including H9 hESC-derived NSC (H9-NSC) and immortalized neural progenitors from fetal brain tissue (hNP), clonal hiNSC lines also express a range of standard NSC markers to varying degrees (FIG. 3C). While there is inherent variability between clonal hiNSC lines, it is also important to recognize the existing variability in expression between these established and commercially available neural cell lines, which suggests that there is not a specific gold standard for distinguishing suitable neural precursor cell lines.

Figure 4:
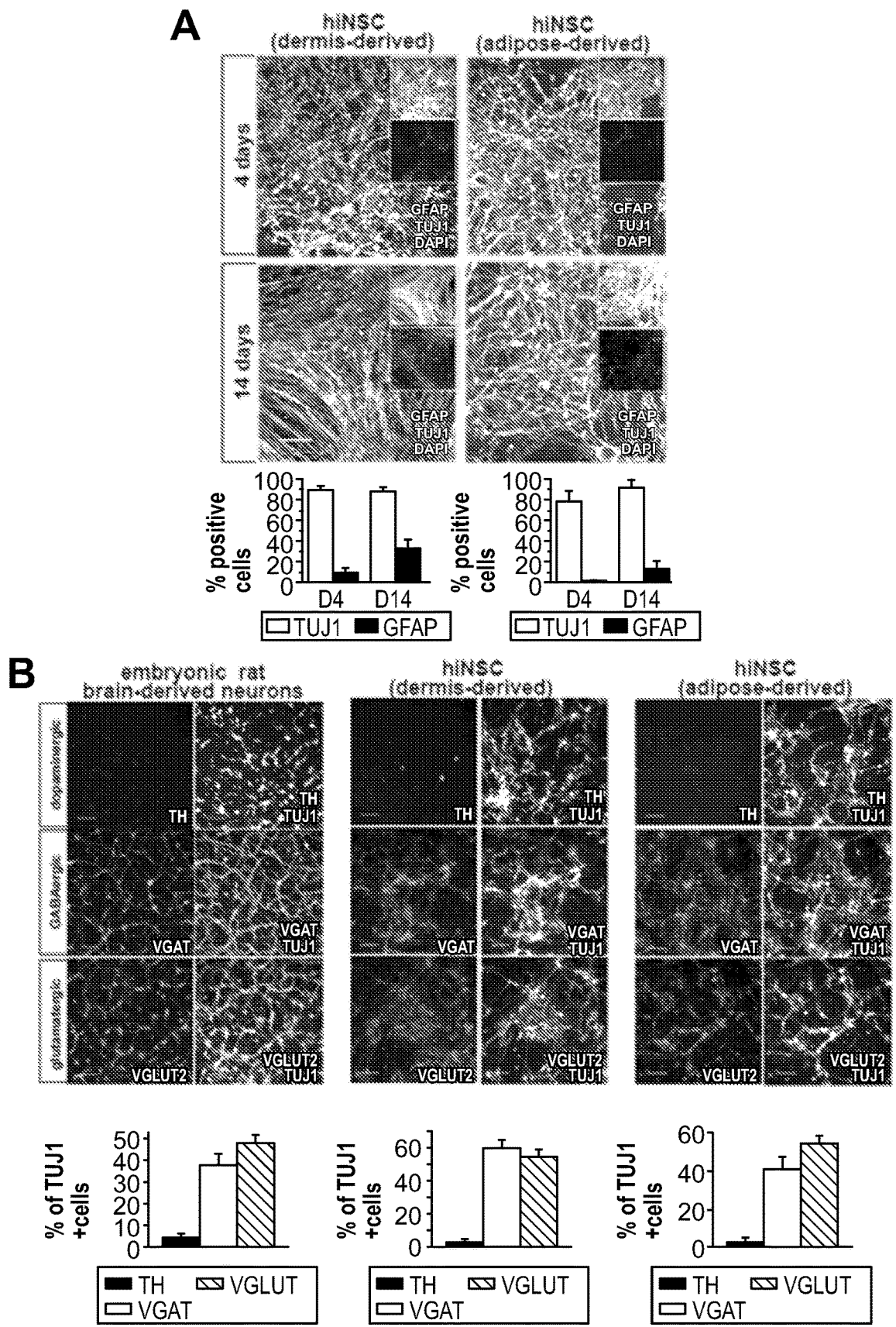
FIGS. 4A-4F show that in some embodiments, hiNSCs are able to rapidly differentiate into neuronal and glial phenotypes.
Figure 4:
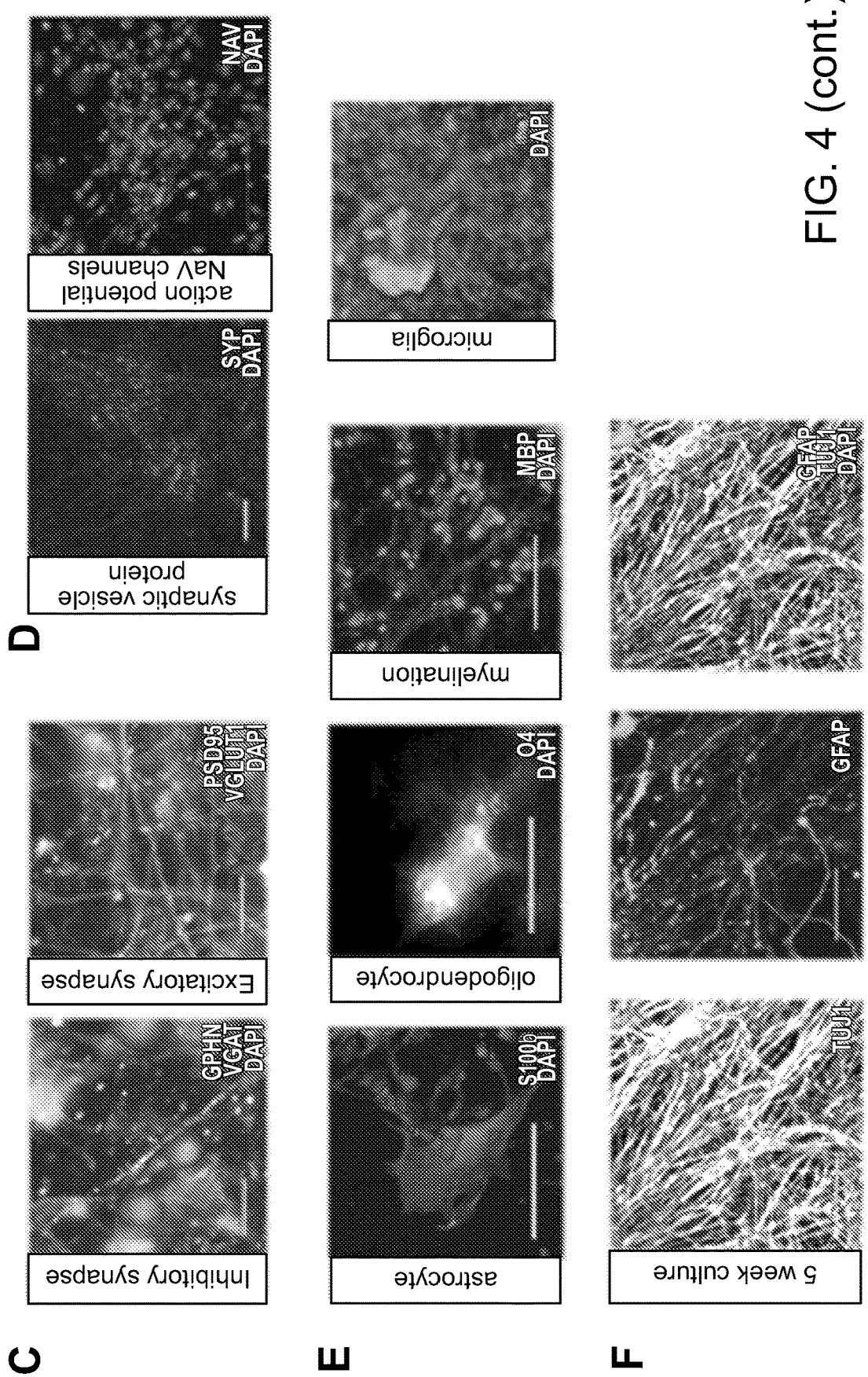
Figure 11:
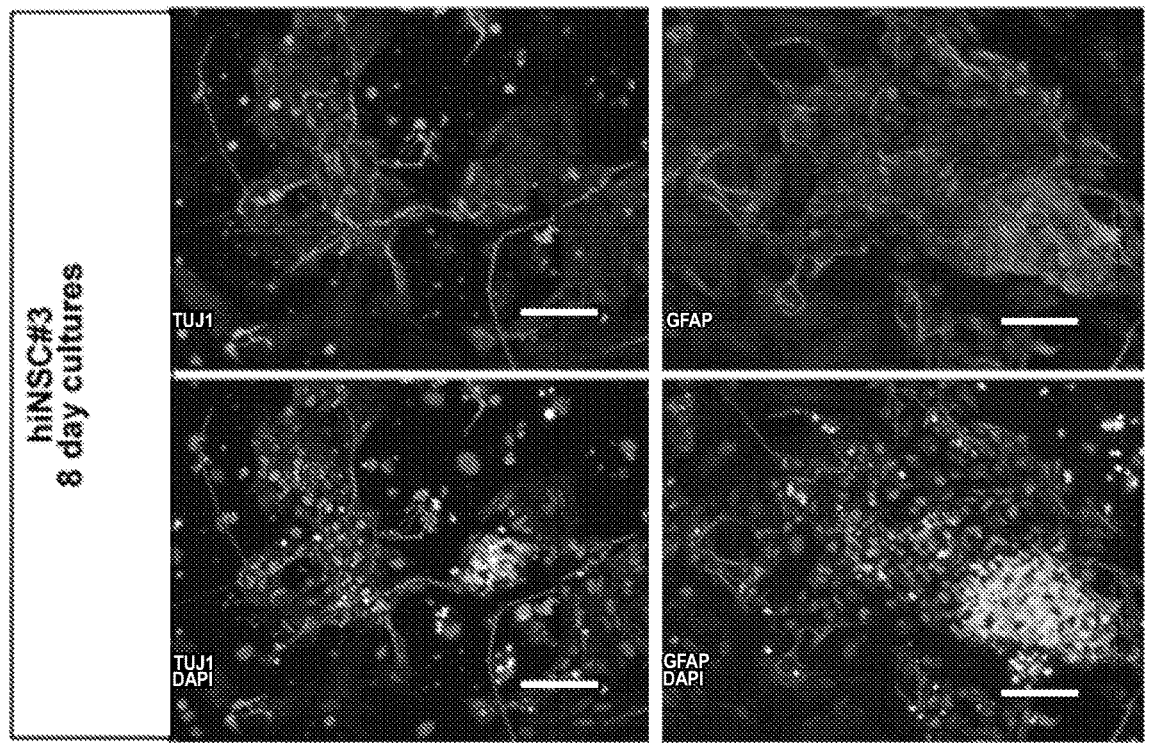
FIGS. 11A and 11B show expression of neuronal (TUJ1) and glial (GFAP) markers in other clonal hiNSC lines, hiNSC #3 (FIG. 11A) and hiNSC #8 (FIG. 11B) after 8 days in culture. Scale bars, 100 μm.
Figure 11:
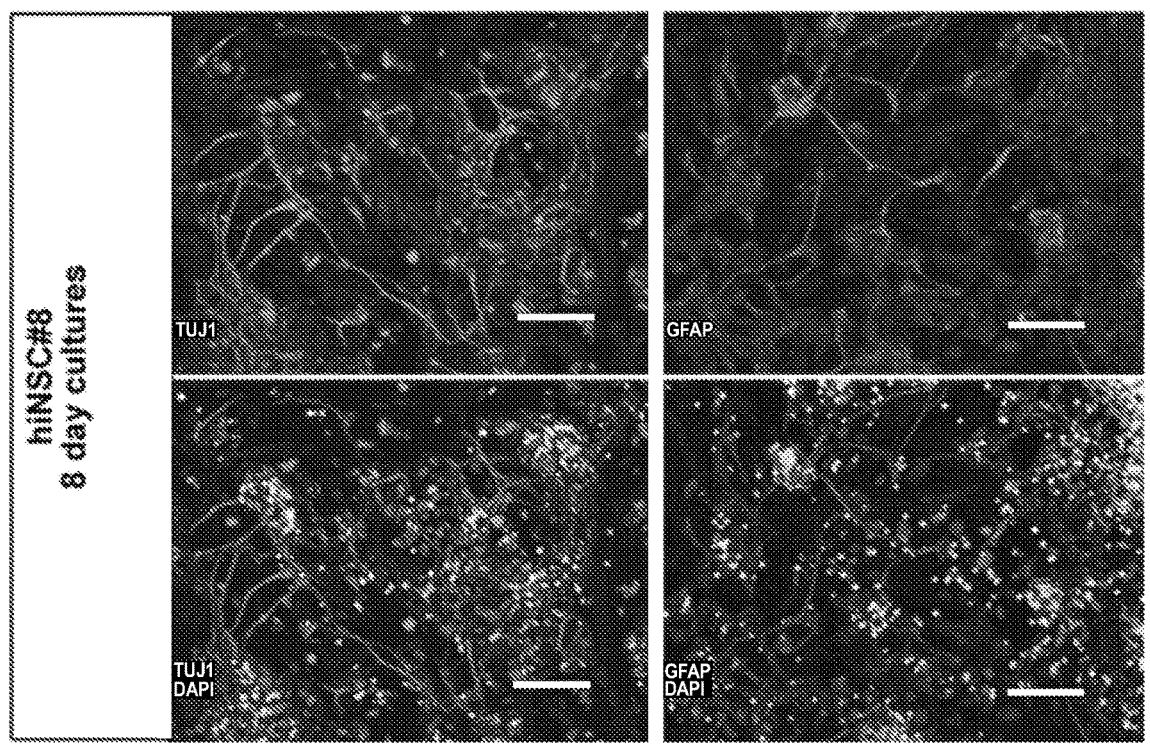
Figure 12:
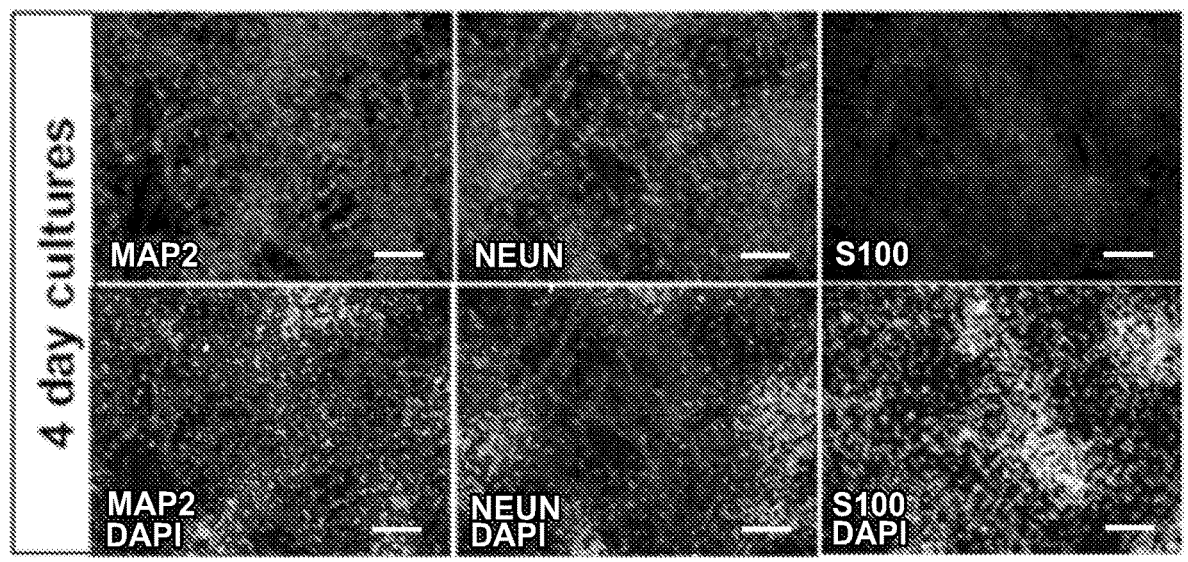
FIG. 12 shows that, in some embodiments, spontaneously differentiated hiNSCs express other neuronal and glial markers including MAP2, NeuN and S100 after 4 (FIG. 12A) and 14 (FIG. 12B) days in culture. Scale bars, 100 μm.
Figure 12:
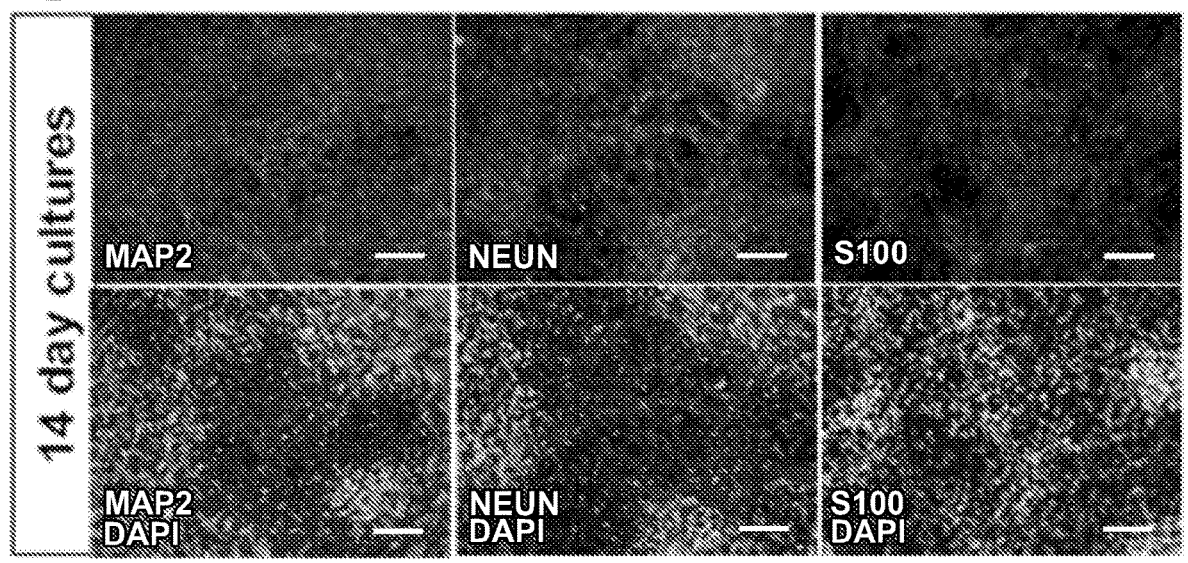
Figure 13:
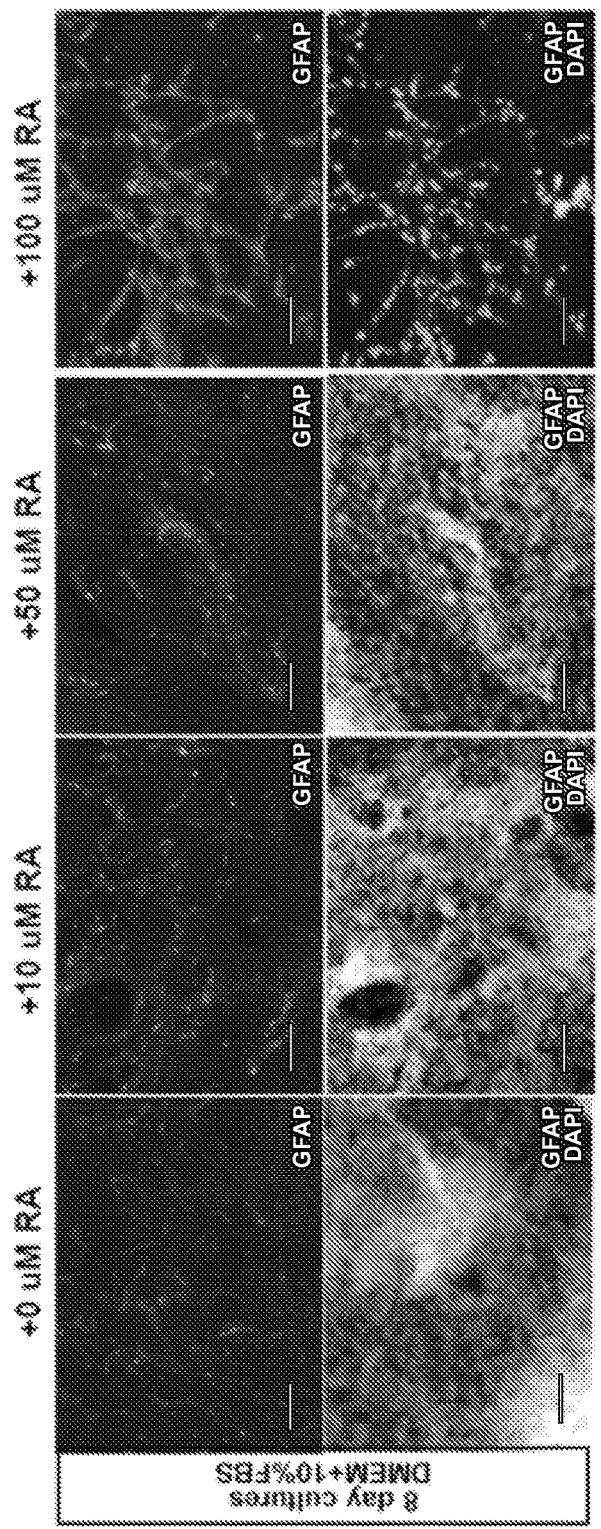
FIGS. 13A and 13B shows that, in some embodiments, hiNSCs spontaneously differentiate into neuronal and glial cell fates, and these can be further directed using growth factors, here, retinoic acid (RA).
Figure 13:
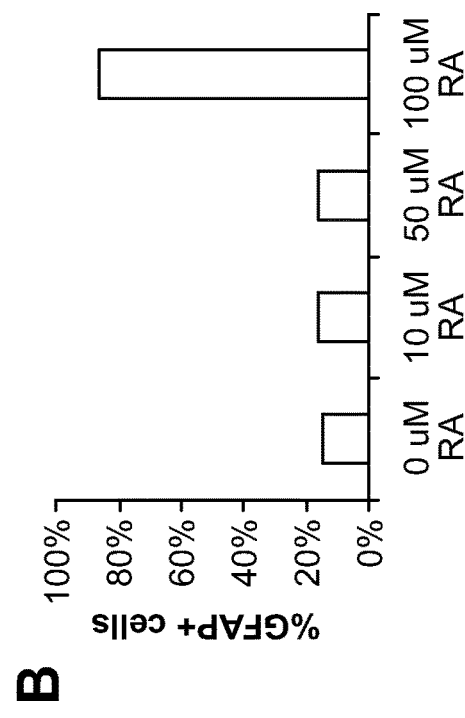

Results—hiNSCs Rapidly and Spontaneously Differentiate into Multiple Neuronal and Glial Subtypes in the Absence of MEF Feeders and FGF Upon removal of hiNSC colonies from feeders, dissociation into single cell suspension, and subsequent culture in low bFGF-containing media, these cells become mostly beta-III tubulin (Tuj1) positive in as few as 4 days (FIG. 4A). They also begin to express glial markers (to varying degrees depending on clonal line). By day 4, hiNSCs derived from neonatal dermal fibroblasts exhibited approximately 89% Tuj1-positive and 9% GFAP-positive cells, which increased to 90% and 33% respectively, by day 14. In hiNSCs generated from adult adipose-derived stem cells, day 4 cells were 78% Tuj1- and 1% GFAP-positive, which increased to 92% and 12% respectively, by day 14. Other spontaneously differentiated hiNSC clonal lines were also mostly neurogenic (FIG. 11). Importantly, spontaneously differentiated hiNSCs also expressed other standard markers of neuronal and glial differentiation including MAP2, NeuN and S100 (FIG. 12). The addition of increasing amounts of retinoic acid to basal media resulted in an increase in GFAP marker expression (FIG. 13), suggesting that while these hiNSCs spontaneously differentiate to neurons and glia, this differentiation can be further directed by the addition of growth factors to generate specific cell types. Taken together, these results demonstrate that provided hiNSC lines rapidly and spontaneously differentiate into mostly a neuronal phenotype in as few as 4 days.

While the high level of expression of pan-neuronal marker Tuj1 is very promising, it is important to further characterize the resulting neuronal phenotypes (FIG. 4B). Rat embryonic neurons (RENs) are a common cell type used in tissue engineering (Tang-Schomer, White et al. 2014). These are derived from E18 rat brain cortices. When cultured under the same media conditions as spontaneously differentiated hiNSCs, RENs mostly stain positive for glutamatergic neurons (48%), followed by GABAergic neurons (37%), while very few stain positive for dopaminergic neurons (4%). Similarly, hiNSCs generated from neonatal dermal fibroblasts and adult adipose-derived stem cells exhibit a relatively high percentage of glutamatergic (55% and 54%, respectively) as well as GABAergic neurons (60% and 40%, respectively).

For a number of tissue engineering applications, it is crucial that cells are sustainable in long term culture. hiNSCs spontaneously differentiated for 5 weeks still express high levels of both Tuj1 and GFAP, and maintain a healthy neuronal morphology with elongated neurite extensions (FIG. 4F). Furthermore, characterization of different subtypes of glial cells revealed the presence of astrocytes (GFAP-positive), oligodendrocytes (O4-positive), myelinated neurons (MBP-positive), and microglia (Iba-1-positive) (FIG. 4E). In summary, provided reprogrammed hiNSCs can differentiate into various subtypes of neurons and glia in as little as four days in culture, and can also be maintained in long term culture. The presence of neurons, astrocytes, and oligodendrocytes demonstrate that reprogramming via provided methods results in tripotent hiNSCs.

Results—Differentiated hiNSCs are Functional In Vitro

Figure 5:
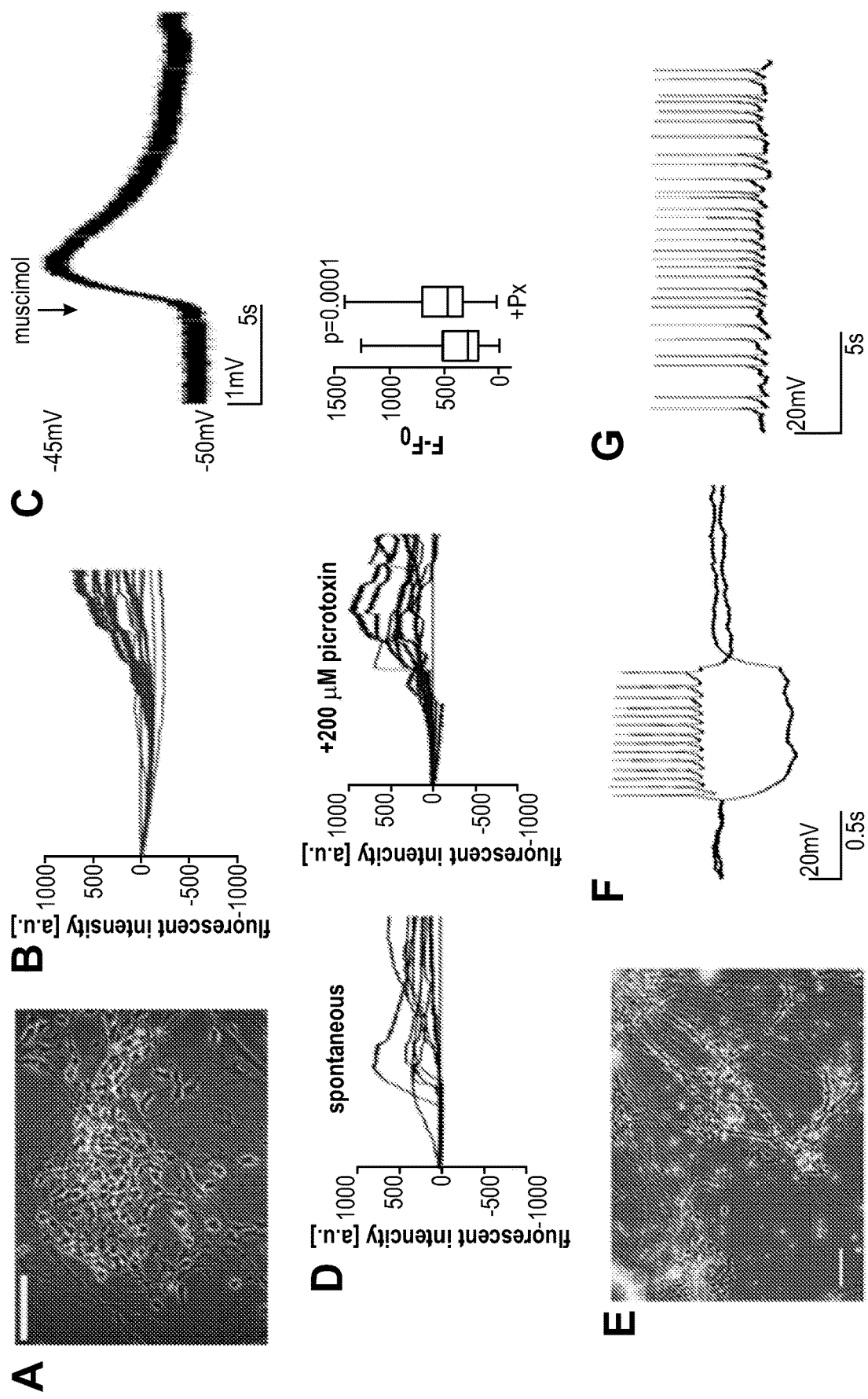
FIGS. 5A-5G show in vitro functionalities of certain embodiments of provided hiNSCs.

While differentiated hiNSCs clearly express various markers of mature neurons and glia within a relatively short period of time, in order to use them for tissue engineering applications it is important to also test functionality. One week post-removal from MEFs, hiNSCs cultured on gelatin substrate appear to have the morphology of immature neurons (FIG. 5A). Fluo-4AM live calcium imaging of these cells reveals that they do have detectable levels of functional calcium signaling at this early time point (FIG. 5B). Furthermore, electrophysiology results reveal that these one-week cultured cells have a resting membrane potential of approximately −50 mV (which corresponds to previously reported Vmem values of immature neurons), and that they demonstrate a depolarizing response to the GABA agonist muscimol (FIG. 5C), which suggests that they have functional GABA receptors, and that they respond in a manner similar to that of typical immature neurons.

Live Fluo-4AM calcium imaging of two-week cultures reveals that spontaneous calcium signaling is increased, and that it is significantly activated in response to picrotoxin, an established blocker of inhibitory GABA receptors (FIG. 5D). Activation of GABA receptors typically inhibits neuronal firing. Picrotoxin blocks these inhibitory GABA receptors thereby causing an increase in neuronal firing. Taken together, hiNSCs cultured for 1-2 weeks respond to well-characterized pharmaceuticals as expected based on studies in animals and in other in vitro neuron systems. Given the short amount of time required to elicit these functional responses, these hiNSCs have future applicability in high throughput drug studies.

The gold standard for in vitro functionality of neurons is the ability to fire action potentials. hiNSCs were cultured on poly-L-lysine coated coverslips for 8 weeks (FIG. 5E), then subjected to electrophysiological analysis. Current clamp recordings showed that the average resting membrane potential of recorded cells was between −50 and −70 mV. Differentiated hiNSCs displayed the ability to generate action potentials in response to depolarizing current steps (FIG. 5F) as well as spontaneous action potentials (FIG. 5G), thereby demonstrating their functionality in vitro.

Results—hiNSCs Migrate, Engraft, and Maintain Neuronal Phenotype In Vivo

Figure 6:
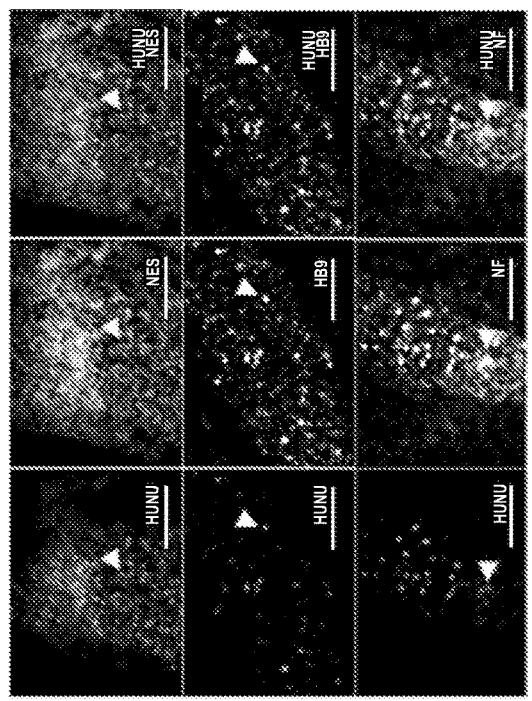
FIGS. 6A-6H shows exemplary injections of provided hiNSCs into certain embryos; hiNSC colonies were removed from feeders, dissociated into single cell suspension, and fluorescently labeled using DiD. hiNSCs were then injected into the lumen of the developing neural tube of ~55 hr old chicken embryos (in ovo). Embryos were then harvested between 1-8 days for subsequent analysis.
Figure 6:
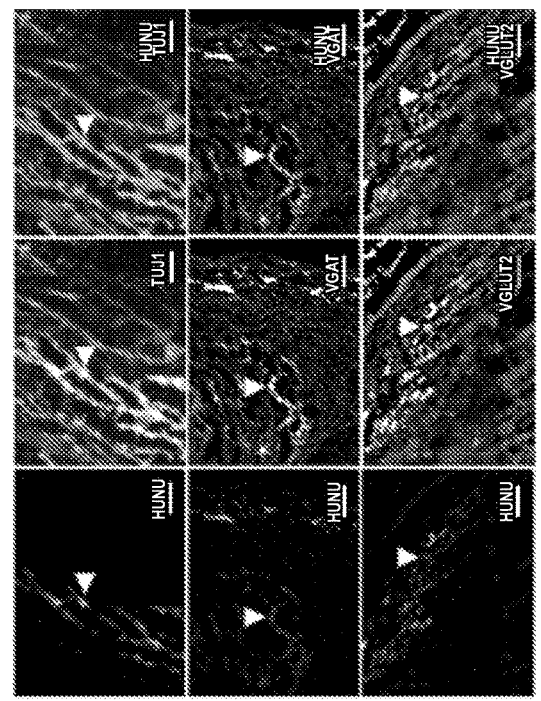
Figure 6:
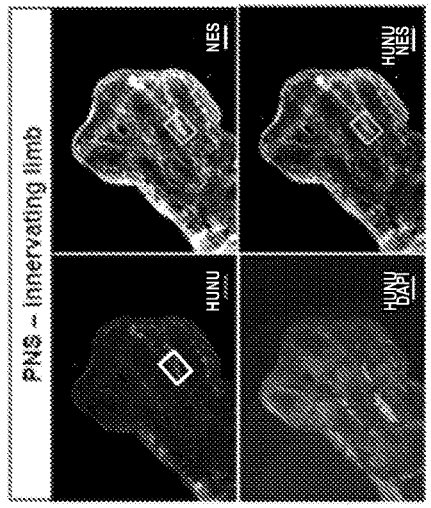
Figure 6:
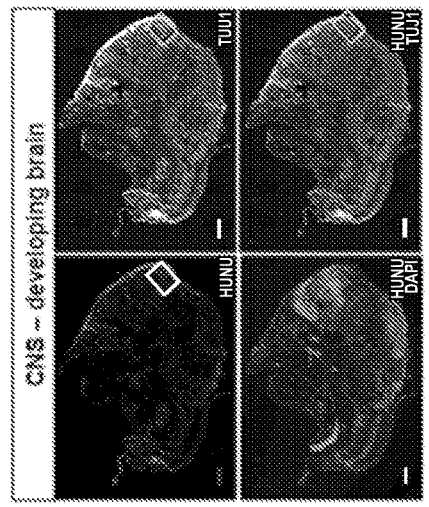
Figure 6:
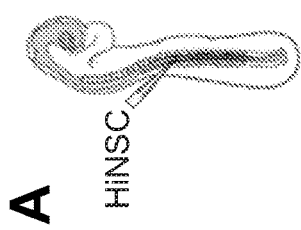
Figure 6:
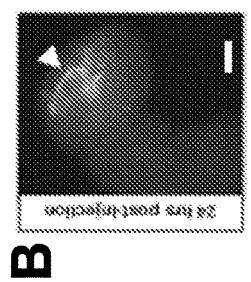
Figure 6:
Figure 6:
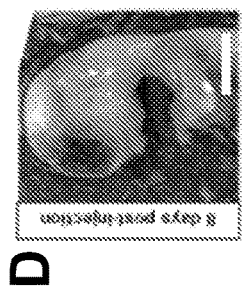
Figure 14:
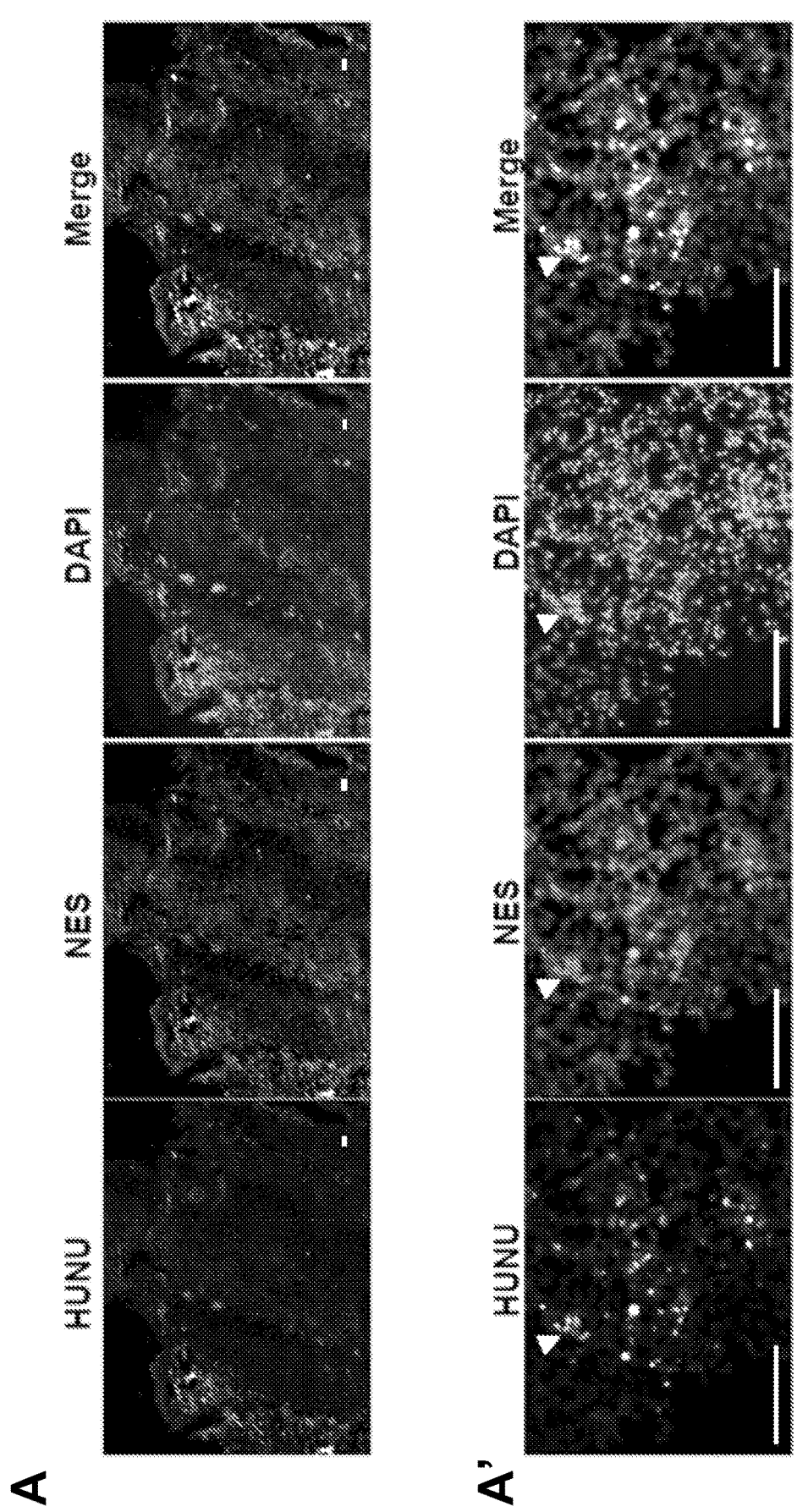
FIGS. 14A and 14B show images of provided hiNSCs injected into early stage chick embryos, and allowed to grow for 6 days.

To assay the ability of hiNSCs to survive and differentiate in vivo, we utilized the embryonic chick model system. Briefly, hiNSCs were dissociated, labeled and injected into the primitive neural tube of a 2.5 day old chicken embryo (FIG. 6A). These embryos were allowed to grow for 1-8 days post-transplantation, then harvested for analysis. After 24 hours, fluorescently labeled hiNSCs can be visualized within the primitive head region (FIG. 6B). Six days after injection of hiNSCs, embryos were harvested and analyzed for incorporation of hiNSCs into the peripheral nervous system (FIGS. 6C, 6E and 6F). Immunostaining results of sagittal cryosections of the developing limb reveal the presence of human cells as indicated by positive staining of human nuclear antigen (HUNU). High magnification images show that these HUNU-positive cells completely co-localize with neural stem cell marker, Nestin as well as with a marker of developing motor neurons (HB9), and neurofilament of sensory and motor axons (NF), suggesting that hiNSCs can contribute to the formation of the peripheral nervous system, and that they maintain their neuronal phenotype even in the presence of a mixed population of non-neuronal cells (FIGS. 6E and 6F). These injected hiNSCs also contribute to the developing spinal region (FIG. 14). Eight days after injection of hiNSCs, embryos were harvested and analyzed for incorporation of hiNSCs into the central nervous system (FIGS. 6D, 6G and 6H). Cryosections of the cranial region show HUNU-positive cells at multiple locations within the developing brain. High magnification images demonstrate that these HUNU-positive cells exclusively co-localize with Tuj1, a more downstream marker of neuronal differentiation, as well as co-localize with neuronal subtype-specific markers VGAT (GABAergic) and VGLUT2 (glutamatergic) (FIGS. 6G and 6H). Importantly, this demonstrates that hiNSCs can contribute to the central nervous system, and can differentiate into neurons in vivo. To our knowledge, this is the first model to demonstrate in vivo incorporation of hiNSCs into both the developing CNS and PNS.

Figure 16:
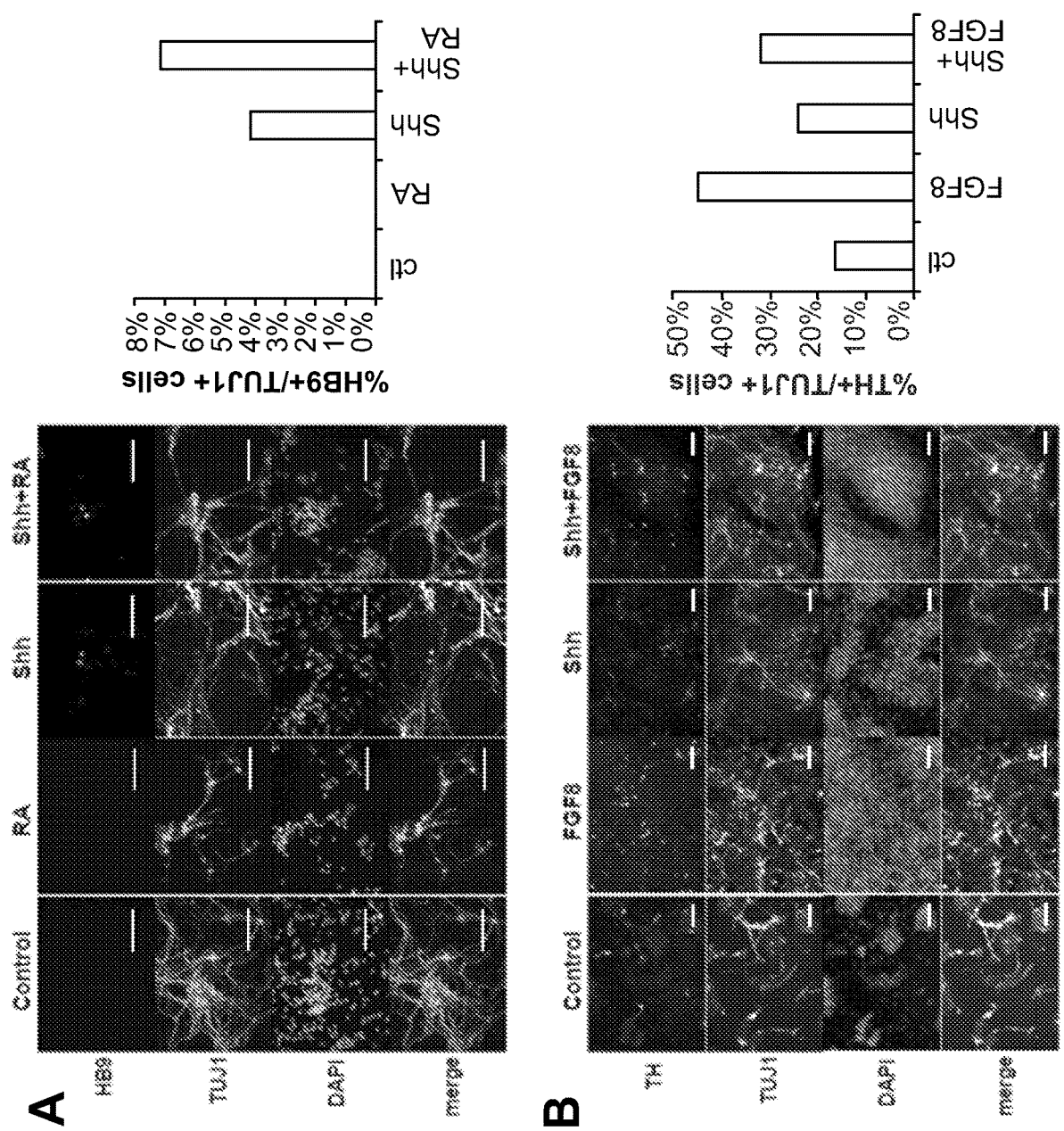
FIGS. 16A and 16B show that hiNSCs can be directed to specific subtypes using growth factors.

Results—hiNSC-Derived Neurons can be Guided to Differentiate into Specific Neuronal Subtypes Further analysis of subtype specification of hiNSCs indicated that after 2 weeks in culture, hiNSCs spontaneously differentiate into mostly glutamatergic and GABAergic neurons, and do not express high levels of the dopaminergic neuron marker TH. While these subtypes were obtained from spontaneous differentiation in generic neurobasal media supplemented with B27, we have shown that differentiation can also be directed. Culturing hiNSCs in the presence of certain combinations of Sonic hedgehog (Shh), FGF8, and/or RA resulted in the upregulation of motor neuron marker HB9, dopaminergic neuron marker TH, or glial marker GFAP (FIGS. 16A and 16B), suggesting that while hiNSCs spontaneously differentiate into neurons and glia, this differentiation can be further guided by the addition of growth factors to generate specific neural and glial subtypes.

Results—hiNSCs have Multiple Application in Tissue Engineering

Figure 7:
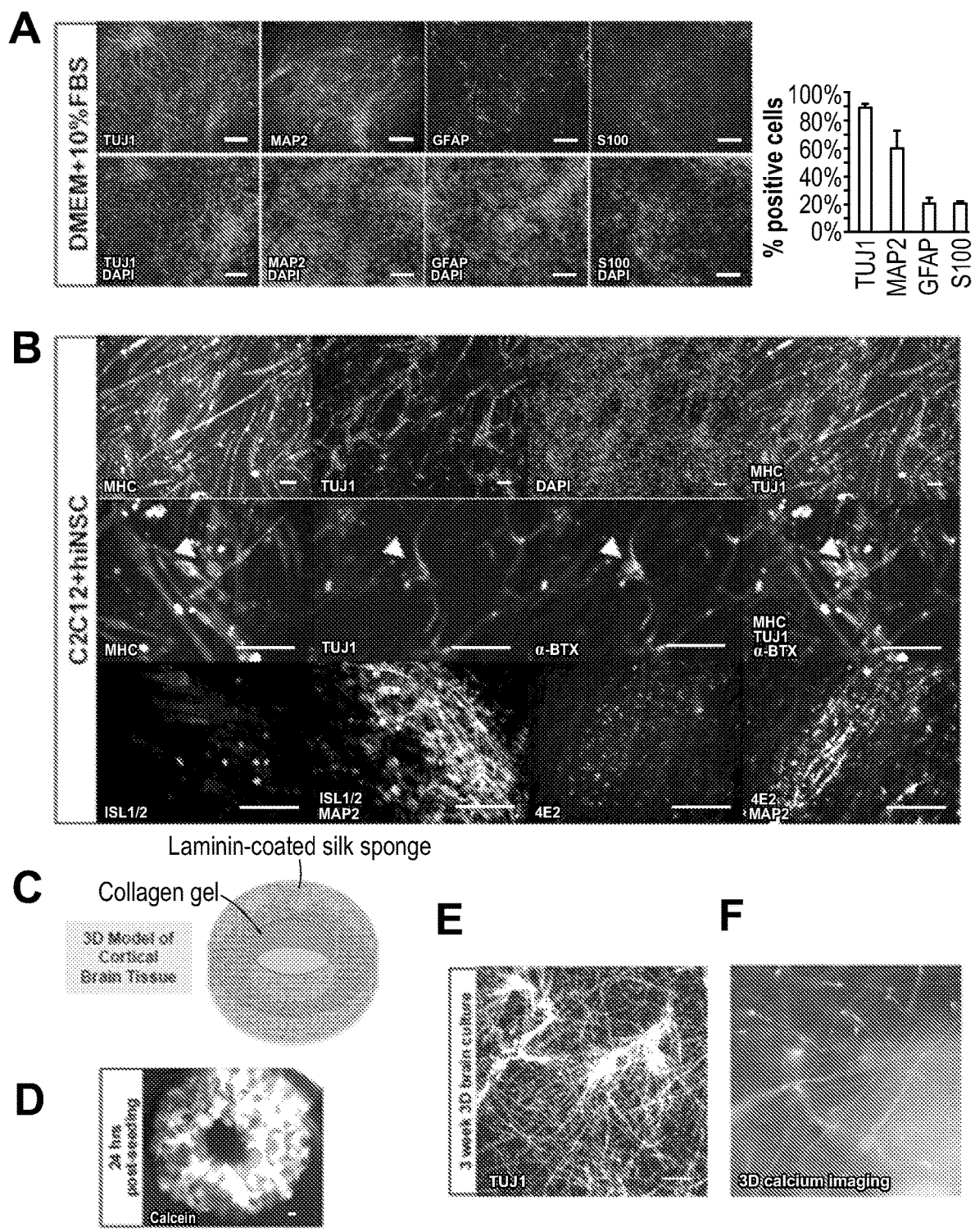
FIGS. 7A-7F depicts, inter alia, exemplary co-culture of provided hiNSCs with other differentiated cell types while still maintaining neuron-specific expression.

In order for cultured human neurons to be successfully incorporated into various tissue engineering models, it is crucial that they maintain their phenotype in multiple cell culture media types and in co-cultures with a variety of differentiated cell types. hiNSCs removed from feeders, dissociated into single cells, then grown in the commonly used culture media DMEM+10% FBS are also mostly neuronal in phenotype (FIG. 7A), with 89% Tuj1+, 60% MAP2+, 20% GFAP+, and 20% S100+. Given this robust neuronal and glial differentiation even in very basic, non-neurogenic media, the data suggests that these hiNSCs can be incorporated into a variety of co-culture models for which FBS is the main supplement. One example of a common cell type grown in FBS-based media is C2C12, an established murine myoblast cell line. C2C12 cells proliferate in DMEM supplemented with 10% FBS, and when grown at high confluence and switched to low serum conditions (1% FBS), cells begin to fuse and form mature skeletal myotubes, which stain positive for myosin heavy chain (MHC). C2C12 cells were grown in co-culture with pre-differentiated hiNSCs in DMEM+1% FBS for 4 days. Immunostaining analysis reveals the presence of differentiated MHC-positive myotubes, as well as non-overlapping expression of Tuj1-positive hiNSCs with neurite extensions (FIG. 7B), suggesting that hiNSCs can be successfully grown in co-culture with other differentiated cell types and still maintain their neuronal phenotype. Furthermore, cocultured hiNSCs expressed motor neuron-specific ISLET1/2 as well as a marker of Schwann cells (4E2), suggesting that the presence of muscle cells may guide the specification of adjacent hiNSCs. Immunostaining also reveals the presence of positive alpha-bungarotoxin (α-BTX) immunostaining, indicative of the presence of nicotinic acetylcholine receptors (AChRs) found in neuromuscular junctions, as well as ISLET 1/2 (transcription factor that promotes motor neuron differentiation) and 4E2 (marker of Schwann cell protein found in regenerating nerves at the site of neuromuscular junctions) (FIG. 7B).

Figure 15:
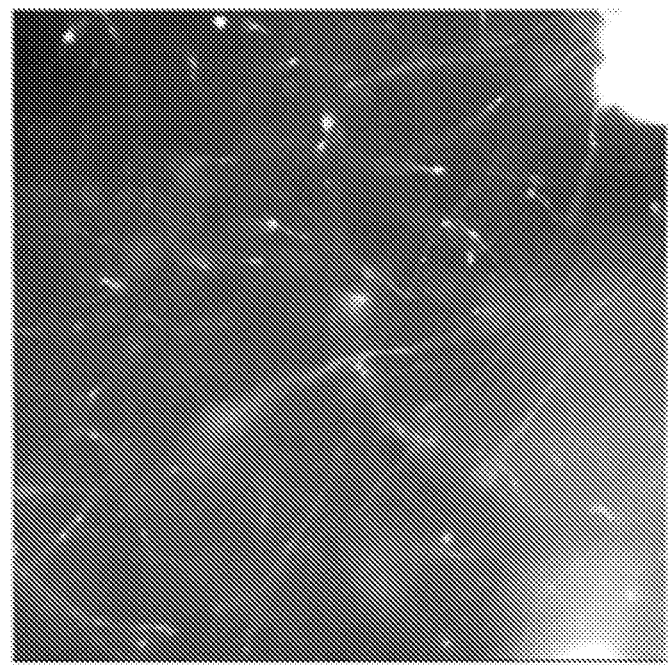
FIG. 15 shows a snapshot from a video of live calcium imaging (using the Fluo4AM calcium indicator) of provided hiNSCs cultured in 3D brain donut model for 2 weeks, showing spontaneous firing between neurons.

Another important application in tissue engineering is to create various models in 3D, as it more fully recapitulates the in vivo condition. In this Example, a three dimensional "donut" brain model was used. The 3D brain model used in this Example consists of an aqueous silk scaffold in which the center is removed to create a "donut" (FIG. 7C). This donut, which serves as the gray matter of the brain, is subsequently coated with laminin, and hiNSCs were seeded and allowed to adhere overnight. Calcein imaging of live cells 24 hours post-seeding of the donut show localization of hiNSCs inside the silk sponge (FIG. 7D). The following day, a collagen gel was added to the center to allow for neurite growth thereby simulating the white matter of the brain. Donuts fixed after three weeks in culture and immunostained for Tuj1 reveal the presence of elongated neurite extensions within the collagen gel (FIG. 7E). Furthermore, hiNSCs seeded into the 3D brain model demonstrated Fluo-4AM calcium signaling (FIG. 7F, a snapshot from a video of live calcium signaling is found in FIG. 15), thereby demonstrating functionality of these neurons in 3D.

Results—hiNSCs Maintain Phenotypic Stability

Analysis of cultures also revealed that hiNSCs were able to proliferate and maintain phenotypic stability over extended periods of time (e.g., several passages). As shown in FIG. 17A, provided cells were able to proliferate for at least 25 passages as shown through Ki67 staining. As shown in FIG. 17B, provided cells expressed neuronal marker Tuj1 for at least 25 passages. FIGS. 17C-17G show all clonal lines tested after 16 weeks in culture expressed the NSC-specific marker Tuj1 and did not express markers of other germ layer lineages (FIGS. 17C-17G), confirming that hiNSCs are and maintain neuroectodermal fate.

Conclusions

This Example describes a novel, simplified protocol for the efficient generation of human induced neural stem cells (hiNSCs) by way of direct reprogramming. Provided reprogrammed hiNSC lines may grow indefinitely as colonies on MEF feeder layers. Like hESCs, hiNSCs stain positive for pluripotent transcription factors Oct4, Sox2 and Nanog, but do not express cell surface markers SSEA4 and Tra-1-81, suggesting that these hiNSC clonal lines are not truly pluripotent. Interestingly, all clonal lines tested showed an increase in endogenous Sox2 expression, but not in endogenous Oct4 expression. Previous studies of various types of NSCs have demonstrated that the maintained expression of Sox2 and the absence of Oct4 is one of the hallmarks of NSCs (Graham, Khudyakov et al. 2003; Mistri, Devasia et al. 2015), which suggests that these hiNSCs are in fact more similar to NSCs than iPSCs.

Figure 17:
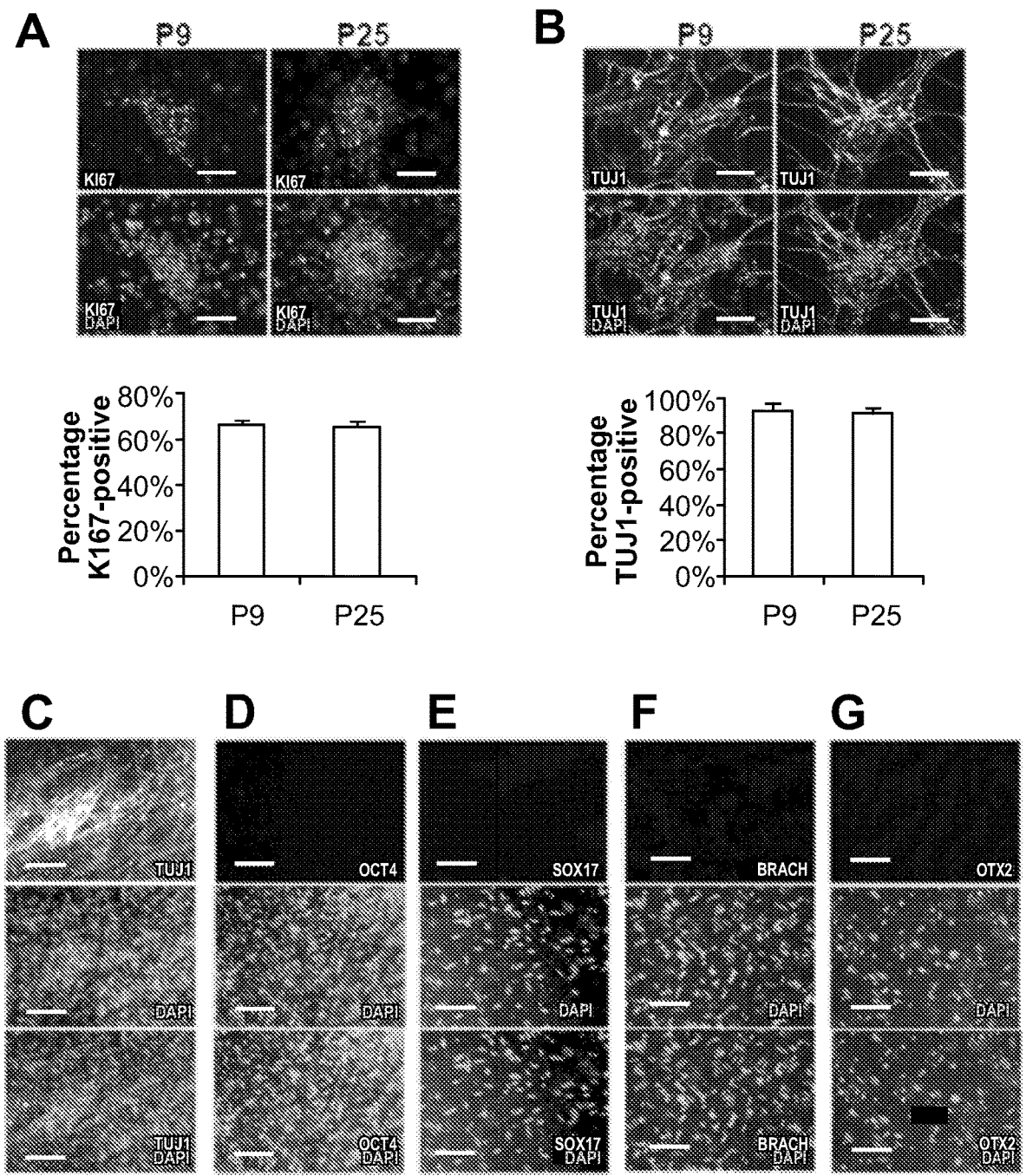
FIGS. 17A-17G show that hiNSCs are able to demonstrate phenotypic stability.

Another criterion of NSCs is the ability to self-renew. Provided hiNSC colonies grown on MEF feeders are approximately 50% positive for proliferation marker Ki67, which is indicative of their vast capacity for self-renewal. Further validation of their NSC phenotype is indicated by the expression of NSC markers, Pax6, Sox1, Nestin and CD133 by immunostaining, as well as other conventional NSC markers quantified by qRT-PCR (see FIG. 3). Gene expression analysis demonstrates that these clonal lines all express detectable levels of these markers to varying degrees. While there may be discernible variability between clonal hiNSC lines, it is important to note that there is also obvious variability between well-established neural cell lines (FIG. 3C, hNPs compared to H9-NSCs), suggesting that there is not a specific gold standard with regard to expression profiles of human NSCs. It is important to note, that all clonal lines tested express NSC-specific markers (to varying degrees) and do not express markers of other germ layer lineages (FIG. 10), suggesting that reprogrammed hiNSC colonies are truly neuroectodermal in fate and are able to maintain their phenotype for extended periods of time, for example, at least 25 passages, as shown in FIG. 17.

As shown in this Example, while provided hiNSC colonies have a seemingly unlimited proliferative capacity, their subsequent capacity for neuronal and glial differentiation may be equally as robust. hiNSC colonies trypsinized and removed from MEF feeders, dissociated into single cell suspension, and subcultured on different substrates begin to differentiate into mostly Tuj1-positive immature neurons and begin to express glial markers (to varying degrees depending on clonal line) in as little as 4 days. At this early timepoint, they also highly expressed differentiated neuron markers MAP2 and NeuN. It is important to mention that there was apparent variability between clonal lines derived from neonatal dermis compared to adult adipose—specifically the dermally-derived hiNSCs generated a higher proportion of glia cells relative to adipose-derived. Without wishing to be held to a particular theory, this discrepancy could be due to the donor cells being neonatal versus adult, the different tissues of origin from which starting cells were harvested, or could be random variability between clonal lines. Regardless, given their rapid and robust capacity for neuronal differentiation, these hiNSC lines would have excellent utility for various high throughput applications such as drug screening assays.

After two weeks in culture, these hiNSCs spontaneously differentiate into mostly glutamatergic and GABAergic subtypes of neurons, and do not express high levels of dopaminergic neuron marker, TH. It is important to note, that these results are obtained from the spontaneous differentiation of these cells, which are cultured in generic neurobasal media supplemented with B27. We have shown that the adding increasing amounts of retinoic acid to basal media results in an increase in glial marker expression (see FIG. 13), and, as described above, have shown that addition of other factors (e.g. RA, Shh, and/or FGF8) can induce differentiation into specific types of neurons when added to basal media. It is also possible that that hiNSCs could be co-cultured with other cell types to induce various types of tissue-specific neurons. For example, Shh has been shown to play a role in the reprogramming of mouse fibroblasts into dopaminergic neuronal progenitors (Caiazzo, Dell'Anno et al., 2011). As described above, the addition of Shh to hiNSC-derived, differentiated cells can induce the formation of a larger proportion of TH-positive neurons (e.g., dopaminergic neurons) as compared to those cultures without Shh.

At later time points, these spontaneously differentiated hiNSCs expressed post-synaptic markers of both inhibitory and excitatory synapses, as well as the synaptic vesicle protein, synaptophysin, suggesting that these cells can form functional synapses. Further evidence of their likely ability to function and fire action potentials is the expression of voltage-gated sodium channels. Not only do provided hiNSCs spontaneously differentiate into various subtypes of neurons, they also differentiate into multiple types of glia cells including oligodendrocytes, myelinated neurons as well as microglia. Interestingly, few hiNSCs to date have demonstrated the ability to give rise to oligodendrocytes during spontaneous differentiation. However, when supplemented with various growth factors such as platelet-derived growth factor (PDGF), PDGF-AA, NT3 and IGF1, neural progenitor cells reprogrammed from human urine cells were able to form O4-positive cells after 3 weeks in culture. Therefore, in some embodiments, provided hiNSCs can be considered multipotent as they possess the ability to generate, inter alia, mature neurons, astrocytes, as well as oligodendrocytes.

While these hiNSCs express various markers of mature neurons and synapses as detected via immunostaining, in order to use them for clinical applications and/or tissue engineering models, it is crucial to validate their functionality. As shown herein, one week post-removal from MEFs, hiNSCs exhibit detectable levels of calcium signaling as well as functional GABA receptors as indicated by a depolarizing response to the GABA agonist, muscimol (see FIG. 5), suggesting that they behave as physiologically immature neurons even at this early timepoint. hiNSCs differentiated for longer periods displayed the ability to generate both current-induced as well as spontaneous action potentials thereby demonstrating their robust functionality in vitro.

While most in vivo studies involve the transplantation of NSCs into the brain of neonatal and/or adult rodent models followed by assay of neural marker expression after several weeks, this Example describes an in vivo model in which the ability of hiNSCs to incorporate into both the central and peripheral nervous systems could be specifically examined. For this reason, we selected the developing chick embryo model. Our study is not the first to utilize a chick embryo model for the purpose of testing neural cell fate determination in vivo. For example, Kharazi et. al. assessed the multipotency of human NSCs isolated from fetal brain transplanted into the lateral ventricle of chicken embryonic brain at the late stage of its development (Hamburger and Hamilton Stage 26)(Hamburger and Hamilton 1951). After 6 days, harvested embryos revealed that these hNSCs were able to engraft into the brain following transplantation (Kharazi, Levy et al. 2013). Another study transplanted mouse ESC-derived motor neurons into lesions made in the developing neural tube of Hamburger-Hamilton stage 15-16 (~55 hr incubation) chick embryos as an alternative method of assaying the ability of in vitro generated neurons to survive and integrate in vivo. Three days after transplantation they demonstrated extensions of the engrafted mouse motor neurons from the spinal cord into the periphery (Wichterle, Peljto et al. 2009). The chick embryo model used in this Example aimed to address both of these tasks. Direct injection of hiNSCs into the lumen of the neural tube expanding throughout the entire cranial to caudal regions allowed for the incorporation of cells into both the head and periphery. This model is more rigorous than other models, as it challenges the cells to maintain their neuronal phenotype even in a microenvironment that may not be conducive to neurogenesis. Intriguingly, all human cells assayed that stained positive for human nuclear antigen (HUNU) exclusively co-localized with Nestin and Tuj1 (N=227). As such, hiNSCs do not appear to demonstrate tumorigenic risk as all of the cells analyzed were positive for NSC or neuronal-specific markers. Furthermore, it is important to note that neural crest cells, the resident cells of the neural tube which develop and migrate out into peripheral tissues, have the capacity to become multiple cell lineages including melanocytes, cartilage, bone, smooth muscle, as well as peripheral and enteric neurons and glia (Le Douarin, Brito et al. 2007). These cell fates are determined at least in part by the extracellular signals in the surrounding microenvironment. When hiNSCs were injected into the neural tube, they exclusively became neuronal in lineage, suggesting that these are specifically neural and do not develop into a non-neuronal fate even when growing in a non-neuronal microenvironment. Therefore, hiNSCs are stably committed to the neural lineage in vivo. To our knowledge, this Example provides the first study to describe human induced NSCs that contribute to both the central and peripheral nervous systems in an in vivo model.

Given the robust capacity of provided hiNSCs, in some embodiments, to maintain neuronal phenotype even under non-neuronal conditions, hiNSCs will therefore have multiple tissue engineering applications. When removed from MEF feeders and subsequently grown in standard non-specific media DMEM+10% FBS, hiNSCs still express over 90% Tuj1+ neurons, suggesting that they do not require neuron-specific media in order to become neurogenic, a feature which has not been explored with other recently described methods of generating induced neural stem cells. This maintenance of neuronal phenotype is very favorable, especially when considering their future use in complex co-cultures in which other cell types may have strict media requirements. As an example of this concept, we co-cultured differentiating C2C12 skeletal muscle cells with hiNSCs, under conditions favorable for the differentiation of the C2C12 cells. Interestingly, both cell types differentiated, expressing their respective markers MHC and Tuj1 in a non-overlapping pattern, suggesting that both cell types can successfully differentiate in co-cultures and maintain their individual phenotypes. Furthermore, these co-cultures also expressed alpha-bungarotoxin visible by immunostaining, which is suggestive of the presence of nicotinic acetylcholine receptors commonly found at the neuromuscular junction. In further support of this finding, these cultures also expressed ISLET 1/2 (transcription factor that promotes motor neuron differentiation) and 4E2 (marker of Schwann cell protein found in regenerating nerves at the site of neuromuscular junctions).

The ability of these hiNSCs to grow and demonstrate functionality in a 3D model is also quite remarkable. We have previously described our 3D brain donut model using embryonic rat brain neurons (Tang-Schomer, White et al. 2014; Chwalek, Tang-Schomer et al. 2015). Other recent studies have developed 3D models for the culture of human neural cells, but these have significant limitations. A 3D human neural cell culture model of Alzheimer's disease was developed that demonstrated characteristic amyloid plaques and neurofibrillary tangles, by overexpressing human β-amyloid precursor protein (APP) and/or presenilin1 (PSEN1) in immortalized human fetal neural stem cells (ReNcell) (Choi, Kim et al. 2014). However, in vitro differentiation of this model required 6-12 weeks, and this technique does not allow for the incorporation of patient-specific cells. Pasca et. al. recently described a 3D model of functional cortical neurons and astrocytes derived from human iPSCs, however, the time required to generate these models (between 52-137 days) makes this type of 3D culture quite prohibitive (Pasca, Sloan et al. 2015). In our 3D brain model seeded with hiNSCs, we see long neurite extensions as early as two weeks, which demonstrate functional calcium signaling (see FIG. 15 for a snapshot of a video of live calcium imaging). These cultures are stable, and have been taken out to 8 weeks with no visible changes in morphology or viability.

Studies have shown that the introduction of these four pluripotent factors under certain conditions yields iPSCs and not iNSCs. This protocol of directly reprogramming somatic cells into hiNSCs differs from the protocol used to generate iPSCs in several ways, of which a few exemplary ways will be further described. First is the use of xeno-free serum replacement. The first hESC lines characterized were cultured on mitotically inactivated MEF feeder layers in media containing FBS (Thomson, Itskovitz-Eldor et al. 1998). This MEF feeder layer is a crucial component in promoting and maintaining the proliferation of undifferentiated hESCs. A commercial serum replacement was developed (Amit, Carpenter et al. 2000) (KO-SR, Invitrogen) that could support the growth of hESC in an undifferentiated state when supplemented with relatively low levels of FGF. The drive to generate suitable iPSCs for potential clinical applications, has resulted in much research toward developing xeno-free reagents free of animal byproducts. Rajala et. al. tested nine different types of xeno-free culture media, and found that none of them were able to maintain the undifferentiated growth of hESCs, demonstrating a decrease in proliferation as well as a loss of an endoderm-specific marker suggestive of a lack of pluripotency (Rajala, Hakala et al. 2007). Without wishing to be held to a particular theory, while the xeno-free KO-SR may contribute to the adoption of a stable non-pluripotent cell fate, another potential reason is the relatively high levels of FGF. The generation of neural progenitors from iPSCs is a multistep process with variable media requirements. Often it involves the initial induction of ectoderm from pluripotent cells, followed by the formation of neural rosettes and/or neurospheres, which are both forms of aggregated neuroectodermal cells. The induction of ectoderm as well as the formation of neural rosettes and stable proliferation in feeder-free cultures has been shown to require very high levels of FGF (100 ng/ml) (Nemati, Hatami et al. 2011). As such, the method of reprogramming hiNSCs described herein results in the formation of colonies that seem to resemble the neural rosette and/or neurosphere stage, which relies mostly on high levels of FGF. Taken together, it seems plausible that the MEF feeder layers are helping to maintain continuous self-renewal of hiNSCs, while the xeno-free serum replacement, which lacks the ability to maintain pluripotency of cells, along with the high levels of FGF, work in combination to promote the neural stem cell fate.

Another possibility is that this reprogramming method preferentially delineates colonies of ectodermal and neuronal origin. Some studies have shown that various iPS lines are predisposed to preferentially becoming cells of their lineage of origin. This might be true in the case of hiNSCs derived from neonatal human fibroblasts as they are also ectodermal in origin. However, we have shown the ability to generate hiNSCs with very similar phenotypes by reprogramming adult human adipose derived stem cells, which are believed to be mesodermal in origin (Minteer, Marra et al. 2013). Taken together, this method of generating hiNSCs has proven successful using starting cell types from two different germ layers in origin. Furthermore, this method eliminates the requirement for specific starting cell types such as CD34+ blood cells as described by other hiNSC reprogramming methods (Wang, Choi et al. 2013; Wang, Choi et al. 2015).

This ability to reprogram multiple starting cell types is not the only distinguishing characteristic of this reprogramming protocol. Importantly, the protocol described herein is very simple and straightforward compared to other methods. While other protocols express some of the same reprogramming factors, namely Oct4, Sox2 and/or Klf4, most if not all previously described methods use them as separate factors. For example, the method described herein shares some similarity with the cell activation and signaling-directed (CASD) strategy of reprogramming previously described by Zhu et. al., in which hiNSCs are created by introducing Oct4, Sox2, Klf4, and shRNA against p53 (Zhu, Ambasudhan et al. 2014; Zhu, Wang et al. 2015) to form a non-pluripotent stable intermediate, which can be driven to adopt a neuroectodermal cell fate by culturing in neurogenic media. As such, there is an increased chance of variability with respect to controlling the relative expression of exogenously introduced genes that can come with using multiple expression vectors. By using a singular polycistronic lentivirus, the relative expression and stoichiometry of the introduced factors is held constant in every round of reprogramming. Furthermore, because the reprogramming media is a defined media that does not contain any FBS, any potential variability associated with differences in FBS quality is also eliminated according to provided methods.

In addition, the subsequent differentiation protocol from hiNSC to neurons and glia is also much simpler than previously described. Many other methods of hiNSC differentiation require an intermediate neurosphere step. For example, primary neurosphere culture was used to enrich induced neural progenitor cells generated from human peripheral blood cells (Lee, Mitchell et al. 2015). Once removed from MEF feeders and cultured as single cells on new substrates, our hiNSCs spontaneously and rapidly differentiate without the requirement of any intermediate steps, thereby bypassing the formation of nonadherent neurospheres. For the purposes of tissue engineering this is a significant advantage of provided methods because once cells have been equilibrated to low adhesion conditions, the transition to adherent monolayer or 3D culture is sometimes difficult, and the center part of neurospheres can often become necrotic.

Another characteristic of some embodiments of hiNSCs reprogrammed by provided methods is the seemingly endless capacity for self-renewal. Many previously described hiNSCs cannot be fully expanded in vitro. For example, serial passaging of neural stem cells generated from hematopoietic progenitors showed a decrease in the level of nestin staining in cells by passage 7 (Wang, Choi et al. 2013; Wang, Choi et al. 2015). As shown herein, clonal hiNSC lines generated by provided methods can be expanded indefinitely as colonies (>30 times to date) and frozen and thawed without any discernible loss in proliferation or capacity for neural or glial differentiation.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

The invention claimed is:

1. A method comprising providing one or more human somatic cells;
   causing transient increased expression of OCT4, KLF4, SOX2, and cMYC in the somatic cells for 2-6 days forming modified somatic cells;
   providing a plurality of inactivated embryonic fibroblasts; and
   contacting the modified somatic cells with the inactivated embryonic fibroblasts in a culture media comprising 20% KO DMEM xeno-free serum replacement and at least 15 ng/ml recombinant bFGF to form human induced neural stem cells.

2. The method of claim 1, further comprising dissociating the human induced neural stem cells from the inactivated embryonic fibroblasts, wherein the dissociation causes the human induced neural stem cells to become at least one of neurons and glial cells.

3. The method of claim 2, wherein the dissociated human induced neural stem cells are exposed to one or more of retinoic acid and 10 ng/ml or less bFGF.

4. The method of claim 2, further comprising associating the dissociated human induced neural stem cells with a plurality of non-neuronal cells.

5. The method of claim 4, wherein the association with non-neuronal cells results in innervation of at least some of the non-neuronal cells.

6. The method of claim 1, wherein the transient increased expression is caused by a vector encoding Oct4, Sox2, Klf4, and cMyc.

7. The method of claim 6, wherein the vector is a polycistronic vector.

8. The method of claim 7, wherein the polycistronic vector is a lentivirus.

9. The method of claim 1, wherein the transient expression is caused by a nucleic acid encoding Oct4, Sox2, Klf4, and cMyc.

10. The method of claim 1, wherein the plurality of inactivated embryonic fibroblasts are inactivated mouse embryonic fibroblasts.

11. The method of claim 1, wherein the human somatic cells are adult human somatic cells.

12. The method of claim 1, wherein the human somatic cells are neonatal human somatic cells.

13. The method of claim 1, wherein the human somatic cells are selected from the group consisting of fibroblasts, adipocytes, dermal cells, epidermal cells, muscle cells, or bone cells.

14. The method of claim 1, wherein the mouse embryonic fibroblasts are inactivated via one or more of mitomycin C treatment and gamma irradiation.

15. The method of claim 1, wherein the OCT4, KLF4, and SOX2, are transiently expressed in approximately a 1:1:1 ratio.

16. The method of claim 1, wherein the human induced neural stem cells are able to be frozen and thawed at least five times and maintain at least a 50% proliferation capacity.

17. The method of claim 1, wherein the human induced neural stem cells may be passaged at least 15 times while associated with the inactivated mouse embryonic fibroblasts without substantial differentiation occurring.

18. The method of claim 1, further comprising associating the human induced neural stem cells with at least one of FGF8, Shh, and RA.

19. The method of claim 18, wherein at least some of the human induced neural stem cells differentiate into motor neurons.

20. The method of claim 18, wherein at least some of the human induced neural stem cells differentiate into dopaminergic neurons.

* * * * *